(12) United States Patent
Pemberton et al.

(10) Patent No.: US 8,507,209 B2
(45) Date of Patent: Aug. 13, 2013

(54) BIOMARKERS

(75) Inventors: Christopher Joseph Pemberton, Christchurch (NZ); Arthur Mark Richards, Christchurch (NZ); Michael Gary Nicholls, Christchurch (NZ); Timothy Grant Yandle, Christchurch (NZ)

(73) Assignee: Otago Innovation Limited, Dunedin (NZ)

(*) Notice: Subject to any disclaimer, the term of this patent is extended or adjusted under 35 U.S.C. 154(b) by 0 days.

(21) Appl. No.: 12/922,444

(22) PCT Filed: Mar. 12, 2009

(86) PCT No.: PCT/NZ2009/000032
§ 371 (c)(1),
(2), (4) Date: Sep. 13, 2010

(87) PCT Pub. No.: WO2009/104974
PCT Pub. Date: Aug. 27, 2009

(65) Prior Publication Data

US 2011/0008808 A1 Jan. 13, 2011

Related U.S. Application Data

(60) Provisional application No. 61/035,761, filed on Mar. 12, 2008.

(51) Int. Cl.
*G01N 33/53* (2006.01)

(52) U.S. Cl.
USPC ............................................. 435/7.1; 436/518

(58) Field of Classification Search
None
See application file for complete search history.

(56) References Cited

U.S. PATENT DOCUMENTS

2005/0244904 A1  11/2005  Ng
2006/0229250 A1* 10/2006  Zhang et al. .................... 514/14

FOREIGN PATENT DOCUMENTS

| WO | WO 2005/052593 | 6/2005 |
|----|----------------|--------|
| WO | WO 2006/131529 | 12/2006 |
| WO | WO 2009/004315 | 1/2009 |

OTHER PUBLICATIONS

A2T3X2_HUMAN GeneBank deposit submitted 2006.*
Wei et al. (Endocrinology 2005, vol. 146, p. 1611-1625).*
Abbott Press Release "New Point of Care Test Helps Physicians Quickly, Accurately Assess Difficult-to-Diagnose Heart Failure at Patient's Bedside" Jul. 26, 2006, retrieved on line on Dec. 13, 2007 at URL: http://www.abbott.com/global/url/pressRelease/en_US/60.5:5/Press_Release_0339.htm.
Bowie, J.U et at., (1990). Deciphering the message in Protein Sequences: Tolerance to Amino Acid Substitutions. Science 247, 1306-1310.
Braud VM, Allan DS, O'Callaghan CA, Soderstrom K, D'Andrea A, Ogg GS, Lazetic S, Young NT, Bell J1, Phillips JH, Lanier LL, McMichael AJ. HLA-E binds to natural killer cell receptors CD94INKG2A, Band C. Nature 1998391:795-799.
Braunwald E, Zipes DP, Libby P. Acute myocardial infarction Chp. 35 Heart disease: a textbook of cardiovascular medicine, 6th ed. 2001. pp. 1114-1231.
Brennan et al., "Preparation of bispecific antibodies by chemical recombination of monoclonal immunoglobulin G1 fragments" Science 229:81-83 (1985).
Chang et al. "Novel Strategy for Indentification of Candidate Cytotoxic T-cell Epitopes from Human Preproinsulin" Tissue Antigens 2003 62:408-417.

(Continued)

*Primary Examiner* — Jacob Cheu
(74) *Attorney, Agent, or Firm* — Acuity Law Group, P.C.; Daniel M. Chambers

(57) ABSTRACT

The invention provides binding agents and assays for ghrelin signal peptide. The agents and assays are useful in methods for predicting, diagnosing, assessing or monitoring acute cardiac disorders, glucose handling disorders and diabetes in a subject. Also provided are nucleotides, polypeptides, and kits useful in the methods of the invention.

40 Claims, 6 Drawing Sheets

(56) References Cited

OTHER PUBLICATIONS

Chenna R, Sugawara H, Koike T, Lopez R, Gibson TJ, Higgins DG, Thompson JD. Multiple Sequence Alignment with the Clustal series of programs Nucleic Acids Res (2003) 31 (13): 3497-500.

Dieguez & Casanueva "Ghrelin: a step forward in the understanding of somatroph cell function and growth regulation" European Journal of Endocrinology 142:413-417.

Gutierrez-Marcos et al. "Atrial natriuretic peptide in patients with accute myocardial infacrtion without functional heart failure" European Heart Journal 1991 12(4): 503-507.

Harlow and Lane 1998. Antibodies: A Laboratory Manual, Cold Spring Harbour Press New York.#.

Hess et al. Pubmed Abstract PMID 15819172 & "N-terminal pro-brain natriuretic peptide (NT-proBNP) in healthy blood donors and in patients from general practitioners with and without a diagnosis of cardiac arrest" Clin. Lab. 2005, 51(3-4): 167-172.

Hoogenboom HR, Winter G (1992) Human antibodies from synthetic repertoires of germline VH gene segments rearranged in vitro. J Mol Biol. Sep. 20, 1992;227 (2):381-8.

Hunt PJ, Richards AM, Nicholls MG, Yandle TG, Doughty RN, Espiner EA. Immunoreactive amino terminal pro brain natriuretic peptide (NT -proBNP): a new marker of cardiac impairment. Clin. Endocrinol. 199747:287-296.

International Search Report for corresponding PCT Application No. PCT/NZ2007/000265 (Mail Date Jan. 9, 2008).

International Search Report for corresponding PCT Application No. PCT/NZ2009/000032 (Mail Date Jun. 23, 2009).

International Search Report for corresponding PCT Application No. PCT/NZ2009/000022 (Mail Date Sep. 21, 2009).

International Search Report for corresponding PCT Application No. PCT/NZ2009/000031 (Mail Date Jul. 9, 2009).

Jernberg T, Stridsberg M, Venge P, Lindahl B. N-terminal pro Brain Natriuretic Peptide on admission for early risk stratification of patients with chest pain and no ST-segment elevation. J. Am. Coll. Cardiology 200240:437-445.

Jones, P.T., Dear, P.H., Foote, J., Neuberger, M.S. and Winter, G. "Replacing the complementarity-determining regions in a human antibody with those from a mouse." Nature (1986) 321: 522-525.

Jung et al. "Elevated concentrations of cardiac troponins are associated with severe coronary artery calcification in asymptomatic haemodialysis patients" Nephrol. Dial. Transplant 2004 19:3117-3123.

Kohler and Milstein 1975. continuous Cultures of Fused Cells Secreting Antibody of Predefined Specificity. Nature, (5517) 256, 495-497.

Kunkel, Thomas A. Rapid and efficient site-specific mutagenesis without phenotypic selection. Proc. Nat!. Acad Sci. USA vol. 82, pp. 488-492, Jan. 1985.

Mehra et al. Pubmed Abstract PMID 15325298 & "Usefulness of elevated B-type natriuretic peptide to predict allograft failure, cardiac allograft vasculopathy and survival after heart transplant" Am. J. Cardiol. 2004 (94(4): 454-458.

Michael Neuberger (1996) Generating high-avidity human Mabs in mice Nature 15 Biotechnology 14,826.

Milstein and Cuello (1983) Hybrid hybridomas and their use in immunohistochemistry, Nature, 305:537-539.

Multiple Sequence Alignment with the Clustal series of programs Nucleic Acids Res (2003) Chapter 5 "Immunizations" pp. 92-117.

National Academy of Clinical Biochemistry and IFCC Committee for standardization of markers of cardiac damage laboratory medicine practice guidelines: analytical issues for biochemical markers of acute coronary syndromes. Circulation 2007 115 :e3 52-e3 5 5.

Non Final Office Action in U.S. Appl. No. 12/381,100, Mail Date Sep. 14, 2010.

Non Final Office Action in U.S. Appl. No. 12/381,100, Mail Date Dec. 3, 2010.

Omland T, Aakvaag A, Bonarjee VV, Caidahl K, Lie RT, Nilsen DW, Sundsfjord JA, Dickstein K. Plasma brain natriuretic peptide as an indicator of left ventricular systolic function and long-term survival after acute myocardial infarction. Comparison with plasma atrial natriuretic peptide and N-terminal proatrial natriuretic peptide. Circulation. 1996 93(11):1963-1969.

Omland T, Persson A, Ng L, O'Brien R, Karlsson T, Herlitz J, Hartford M, Caidahl K. Ntenninal pro-B-type natriuretic peptide and long-term mortality in acute coronary syndromes. Circulation. 2002 106:2913-2918.

Pemberton CJ, Johnson ML, Yandle TG, Espiner EA. Deconvolution Analysis of the Secretion and Elimination of Cardiac Natriuretic Peptides During Acute Volume Overload. Hypertension 2000;36: 355-359.

Poykko SM, Kellokoski E, H5rkk5 S, Kauma H, Kesaniemi YA, Ukkola O. Low plasma ghrelin is associated with insulin resistance, hypertension, and the prevalence of type 2 diabetes. Diabetes. Oct. 2003;52(10):2546-53.

Reyzer et al. "MALDI Mass Spectrometry for Direct Tissue Analysis: A New Tool for Biomarker Discovery" Journal of Proteome Research 2005 4:1138-1142.

Richards AM, Nicholls MG, Troughton RW, Lainchbury JG, Elliott J, Frampton C, Espiner EA, Crozier IG, Yandle TG, Turner J. Antecedent hypertension and heart failure after myocardial infarction. J. Am. Coll. Cardiology. 2002 39: 1182-1188.

Richards AM, Nicholls MG, Yandle TG, Frampton C, Espiner EA, Turner JG, Buttimore RC, Lainchbury JG, Elliott JM, Ikram H, Crozier IG, Smyth DW. Plasma N-terminal pro-brain natriuretic peptide and adrenomedullin: new neurohormonal predictors of left ventricular function and prognosis after myocardial infarction. Circulation 1998 97:1921-1929.

Riechmann L, Clark M, Waldmann H, Winter G. Reshaping human antibodies for therapy. Nature. Mar. 24, 1988;332(6162):323-7.

Skyler JS. Non-insulin-dependent diabetes mellitus: a clinical strategy~ Diabetes Care. May Jun. 1984;7 SupplIL118-29.

Solberg H. Approved recommendation (1987) on the theory of reference values. Part 5. Statistical treatment of collected reference values. Determination of reference limits. Journal of clinical Chemistry and Cilinical Biochemistry 198725:645-656.

Squire IB, O'Brien RJ, Demme B, Davies JE, Ng LL. N-terminal pro-atrial natriuretic peptide (N-ANP) and N-terminal pro-B-type natriuretic peptide (N-BNP) in the prediction of death and heart failure in unselected patients following acute myocardial infarction. Clin Sci (Lond). 2004107(3):309-316.

Suresh, M. R., Cuello, A. C. and Milstein, C. (1986) Bi-specific monoclonal antibodies from hybrid hybridomas. Methods in Enzymology, 121: 210-228.

Tapanainen JM, Lindgren KS, Makikallio TH, Vuolteenaho 0, Leppaluoto J, Huikuri HV. Natriuretic peptides as predictors of non-sudden and sudden cardiac death after acute myocardial infarction in the beta-blocking era. J Am Coll Cardiol. 200443(5):757-763.

The Immunoassay Handbook. 3rd edition, ed. David Wild. Elsevier Ltd, 2005, pp. 103, 121-126.

Thibault G, MUlihy KK, Gutkowska J, Seidah NG, Lazure C, Chretien M, Cantin M. NH2-terminal fragment of rat pro-atrial natriuretic factor in the circulation: identification, radioimmunoassay and half-life. Peptides. 19889:47-53.

Tristan J. Vaughan, Jane K. Osbourn & Philip R. Tempest (1998) Human antibodies by design. Nature Biotechnology 16,535-539.

Troughton RW, Frampton CM, Yandle TG, Espiner EA, Nicholls MG, Richards AM. Treatment of heart failure guided by plasma amino-telminal brain natriuretic peptide (N-BNP) concentrations. Lancet 2000355: 1126.1130.

Troughton RW, Prior DL, Pereira JJ, Martin M, Fogarty A, Morehead A, Yandle TG, Richards AM, Starling RC, Young JB, Thomas JD, Klein AL. Plasma B-type natriuretic peptide levels in systolic heart failure: Importance of left ventricular diastolic function and right ventricular systolic function. J Am Coll Cardiol. 2004 43 :416-422.

Universal definition of myocardial infarction. Consensus statement from the Joint 5 ESC/ACCF/AHA/WHF Taskforce for the redefinition of myocardial infarction. Circulation 2007 116:2634-2653.

Verhoeyen M. C Milstein, and G Winter Reshaping human antibodies: grafting an anti lysozyme activity. Science Mar. 25, 1988;239(4847):1534-6.

* cited by examiner

| Peptide | Cross reactivity with Ghr-SPn(1-9) antiserum (%) |
| --- | --- |
| Ghr-SPn(1-9) | 100 |
| proBNP(1-13) | <0.003 |
| proBNP(1-76) | <0.01 |
| proANP(1-30) | <0.009 |
| Insulin | <0.003 |
| IGF-I | <0.002 |
| IGF-II | <0.006 |
| ANP | <0.008 |
| BNP | <0.009 |
| Endothelin 1 | <0.006 |
| Angiotensin II | <0.003 |
| Angiotensin(1-7) | <0.01 |
| Urotensin II | <0.003 |
| CNP | <0.006 |
| Ghrelin | <0.007 |
| C-Ghrelin | <0.01 |
| proCNP(1-15) | <0.008 |
| Adrenomedullin | <0.01 |
| Urocortin I | <0.01 |
| Urocortin II | <0.01 |
| BNP-SPn(1-10) | <0.001 |
| ANP-SPc(16-25) | <0.001 |
| ANP-SPn(1-10) | <0.001 |
| INS-SPn(1-9) | <0.001 |
| Clopidigrel | 0 |
| Morphine | 0 |
| Aspirin | 0 |

Figure 7

```
Rattus norvegicus        MVSSATICSLLLLSMLWM-DMAMA
Homo sapiens             MPSPGTVCSLLLLGMLWL-DLAMA
Ovis aries               MPAPRTIYSLLLLSLLWM-DLAMA
Sus scrofa               MPSTGTICSLLLLSVLLMADLAMA
Mus musculus             MLSSGTICSLLLLSMLWM-DMAMA
Canis lupus familiaris   MPSLGTMCSLLLFSVLWV-DLAMA
Felis catus              MPSPGTVCSLLLFSMLWA-DLAMA Consensus                MPSPGTICSLLLLSMLWMADLAMA
```

Figure 8

BIOMARKERS

This application is a US national stage of PCT/NZ/2009/000032 filed on Mar. 12, 2009 which claims the benefit of U.S. Provisional Application Ser. No. 61/035,761 filed on Mar. 12, 2008; the contents of each of which is incorporated herein by reference in its entirety.

FIELD OF THE INVENTION

This invention relates to ghrelin signal peptide (GRN-SP) and its use in the prognosis, diagnosis and monitoring of biological events or disorders or states which result in release of the marker into the circulation. Such states include obesity and associated conditions such as glucose handling disorders, diabetes and cardiovascular disease, particularly acute cardiac disorders.

BACKGROUND

Obesity is at epidemic proportions in the human population. It is one of the leading causes of preventable death in the Western world. The World Health Organisation (WHO) recognises obesity as one of the top 10 global health problems.

The causes of obesity in a population may be attributed to a variety of genetic and social factors. But at a fundamental level, obesity will develop when energy intake exceeds energy use. Obese individuals are at risk of developing associated conditions such as diabetes and cardiovascular disease, particularly acute cardiac disorders.

Diabetes Mellitis is a metabolic disorder characterized by deficiencies in insulin secretion, insulin action or both. These deficiencies result in chronic hyperglycemia. Diabetes affects over 170 million people worldwide, and is expected to double in the next twenty years.

Diabetes is divided into two types known as Type 1 diabetes and Type 2 diabetes. Type 1 diabetes is an autoimmune related disorder where the immune system of the individual acts to destroy the beta cells of the pancreas. Individuals with Type 1 diabetes are generally insulin dependent. They exhibit limited insulin secretion, if any.

Type 2 diabetes is the most common form, accounting for 90 to 95% of cases. The majority of Type 2 diabetics are not insulin dependent, but exhibit insulin secretion and insulin action deficiencies leading to hyperglycemia. The hyperglycemia is often mild with symptoms difficult to recognise.

As a result, many Type 2 diabetics go undiagnosed for many years. At any given time it is estimated that 15-20% of the population may be at risk of developing Type 2 diabetes, but are undiagnosed.

Diabetes is most commonly diagnosed based on the oral glucose tolerance test which assesses glucose handling. Individuals are given a glucose drink after overnight fasting to test their tolerance for glucose. The test takes several hours to measure responses. Unfortunately, the glucose tolerance test and fasting insulin level test suffer from a lack of sensitivity, and false positives which limit their usefulness as prognostic indicators of diabetes.

Obesity is also a significant risk factor for cardiovascular disease, increasing the risk of a cardiac event by two to three times. Despite the recognised need for diagnostic and prognostic tools for assessing the risk of an individual developing diabetes or precursor glucose handling disorders, and associated conditions such as cardiovascular disease, no simple and accurate tests are available.

Early diagnosis and ongoing assessments of diabetes and precursor glucose handling disorders, or any other form of dysglycemia or dysinsulinemia, are important not only for the management thereof, but also for managing associated conditions, such as cardiovascular disease. In addition to providing early detection methods for conditions, diseases and disorders associated with dysglycemia or dysinsulinemia, for example, the present invention also has broader applications in the cardiovascular area.

Acute cardiac disorders including acute coronary syndromes (ACS) encompass a wide spectrum of cardiac ischemic events ranging from unstable angina through to acute myocardial infarction (AMI). AMI presents as the most serious of these events and therefore requires rapid and accurate diagnosis. Patients who present with two or more of the described features (a history of ischemic chest discomfort, evolutionary changes on serial electrocardiogram (ECG) traces and a rise and fall in plasma cardiac biomarkers) are clearly identified as undergoing AMI.[26] However, a significant proportion of patients (40%-50%) who present with suspected AMI do not have serial changes on ECG, or typical symptoms thus placing heavy emphasis on circulating biomarker concentrations for accurate diagnosis.[26,27]

Accurate early diagnosis of myocardial infarction facilitates prompt introduction of reperfusion treatment, including effective percutaneous or thrombolytic revascularisation and adjunctive anticoagulant and anti-platelet therapy. Such treatments are progressively less effective at reducing mortality and morbidity with each hour of delay in diagnosis and management.[2-4] Given the need for accelerated decision-making in this clinical situation, there is a need for identification of circulating biomarkers providing an early and specific diagnosis of acute cardiac disorders, particularly AMI, for example.

Indeed current clinical guidelines highlight the importance of biomarker measurement in the identification of myocardial infarction and acute coronary syndromes.[26] A number of biomarkers have been proposed for this purpose, including creatine kinase-MB (CK-MB), troponin T (TnT), troponin I (TnI) BNP, N-BNP (also known as NP-BNP), BNP signal peptide (BNP-SP) and myoglobin, but there are limitations to their use. Time to detectable or abnormal elevation of plasma cardiac biomarkers can be up to 6 hours (myoglobin, CK-MB) to 12 hours (TnT, TnI, BNP, N-BNP) with peak levels not occurring until 24-48 hours after onset of injury, imposing a window of delay upon precise diagnosis and treatment.[1-4] Furthermore, both myoglobin and CK-MB are non-specific and can be secreted from extra-cardiac sources, especially during trauma or surgery.[1]

The long term diagnostic/predictive powers of the known markers therefore lack the accompanying power of a specific marker providing early specific diagnosis of acute cardiac disorders such as acute cardiac injury within the first few hours of clinical presentation. A need thereof still exists for early markers.

It is a further object of the present invention to provide an early marker of acute cardiac disorders, and/or to at least provide the public with a useful choice.

SUMMARY OF THE INVENTION

Human ghrelin signal peptide (GRN-SP) is a 23 amino acid peptide cleaved from ghrelin (preproghrelin) (1-117) SEQ ID NO:1. Processing of human preproghrelin is shown in FIG. 5. GRN-SP (1-23) is shown separately in SEQ ID NO:15.

The applicants have found for the first time that the ghrelin signal peptide GRN-SP and fragments thereof are released into the circulation. Useful circulating biomarkers are identified and provided. Previously it was thought that GRN-SP was only ever produced intracellularly.[25]

Based on this finding, the applicants provide in one aspect of the invention a method for predicting, diagnosing, assessing or monitoring a biological event or disorder in a subject wherein the event correlates with the release of one or more GRN-SP biomarkers into the circulation, the method comprising measuring the level of one or more GRN-SP biomarkers in a sample taken or derived from the subject, and analysing the level in conjunction with a reference value or range for said one or more biomarkers.

In one embodiment, the GRN-SP biomarker is a GRN-SP. In another embodiment, the GRN-SP biomarker is a GRN-SP fragment. In one preferred embodiment, the GRN-SP fragment is human GRN-SP (1-9) SEQ ID NO:17).

In another embodiment, the method comprises comparing the level of a GRN-SP biomarker, preferably a GRN-SP fragment, in one or more samples taken or derived from the subject with the GRN-SP biomarker level from a control wherein a deviation in the measured level from the control level is indicative of a biological event or disorder.

In a diabetic subject such as a type 1 diabetic subject, or a subject with another dysglycemia resulting from depressed insulin secretion levels, the level of ghrelin will be different than normal as will GRN-SP and/or GRN-SP fragment levels. This finding indicates that GRN-SP is useful as a marker for such conditions. Depending on the insulin state of the subject GRN-SP biomarker levels in the subject will be higher or lower than normal.

In a diabetic subject, such as a type 2 diabetic subject, or in a subject with another dysinsulinemia, the level of ghrelin will be higher than normal, as will GRN-SP and/or GRN-SP fragment levels. This finding indicates that GRN-SP and/or GRN-SP fragments are also useful as a marker for such conditions, as well as in other hyperinsulinemic states such as metabolic syndrome. Depending on the insulin state of the subject GRN-SP biomarker levels in the subject will be higher or lower than normal.

Accordingly, in another aspect the present invention provides a method for predicting, diagnosing, assessing or monitoring diabetes or diabetic potential, as well as other conditions characterised by dysglycemia and/or dysinsulinemia, the method comprising measuring the level of GRN-SP biomarkers in a sample taken or derived from the subject, and analysing the level in conjunction with a respective reference value for said one or more biomarkers.

In another embodiment, the method comprises comparing the level of an GRN-SP biomarker, preferably an GRN-SP fragment, in one or more samples taken or derived from the subject with the GRN-SP biomarker level from a control wherein a measured level of GRN-SP which deviates from the control level is indicative of diabetes or a predisposition to diabetes, or another condition associated with dysglycemia and/or dysinsulinemia. In one embodiment the GRN-SP biomarker levels may be lower than the control.

The invention also provides a method of assessing glucose handling in a subject, the method comprising:
  (a) measuring the level of a GRN-SP biomarker, preferably a GRN-SP fragment, in a subject after administration of glucose;
  (b) comparing the level of said GRN-SP with the GRN-SP from a control, wherein a deviation in the measured level of GRN-SP from the control level is indicative of a glucose handling disorder.

The applicants have also surprisingly discovered that the circulating concentration of GRN-SP biomarkers is highest in the first few hours following onset of, or at clinical presentation with suspected acute coronary syndromes (ACS). Peaks are in the order of, for example, 1.5 to five times higher, commonly two to three times higher, than normal control populations in these first hours.

Accordingly, in a further aspect the present invention provides a method for predicting, diagnosing or monitoring an acute cardiac disorder (ACD) in a subject, the method comprising measuring the level of a GRN-SP biomarker, preferably a GRN-SP fragment, in a biological sample from the subject and comparing the level of said GRN-SP biomarker with the GRN-SP and/or GRN-SP fragment level from a control or reference value or value range wherein a measured level of the GRN-SP biomarker higher than the control level or predetermined reference value or value range is indicative of ACD.

The invention also provides a method for monitoring a response to treatment of a biological event or disorder, particularly acute cardiac disorder (ACD) in a subject, the method comprising measuring the level of a GRN-SP biomarker, preferably a GRN-SP fragment, in a sample taken or derived from the subject and comparing the level of said GRN-SP biomarker with the GRN-SP biomarker level from a control or a reference value or value range, wherein a change in the measured level of GRN-SP from the control level, or a predetermined reference value or value range, is indicative of a response to the treatment.

In another aspect, the invention also provides a method for predicting, diagnosing or monitoring a cardiac transplant rejection episode in a subject, the method comprising measuring the level of a GRN-SP biomarker, preferably a GRN-SP fragment, in a sample taken or derived from a subject after heart transplant and comparing the level of said GRN-SP biomarker with the GRN-SP biomarker level from a control or reference value or value range, wherein a measured level of the GRN-SP biomarker higher than the control level, or reference value or value range, is indicative of transplant rejection or a transplant rejection episode.

The invention also provides a method of distinguishing between a pulmonary disorder and an acute cardiac disorder (ACD) in a subject, the method comprising measuring the level of a GRN-SP biomarker, preferably a GRN-SP fragment, in a sample taken or derived from the subject, and comparing the level of said GRN-SP biomarker with the GRN-SP biomarker level from a control, or reference value or value range, wherein a measured level of GRN-SP biomarker higher than the control level, or reference value or value range, is indicative of ACD.

The invention also provides a method for predicting, diagnosing or monitoring an acute cardiac disorder (ACD), cardiac transplant rejection, or ACD/pulmonary disorder in a subject, the method comprising measuring the level of a GRN-SP biomarker, preferably a GRN-SP fragment, in a sample taken or derived from the subject within about the first six or four hours of onset of, or clinical presentation with ACD, cardiac transplant rejection or ACD/pulmonary disorder comparing the measured level of the GRN-SP biomarker with the GRN-SP biomarker level from a control, or reference value or value range, wherein a measured level of the GRN-SP biomarker higher than the control level, or reference value or value range, is indicative of ACD or a cardiac transplant rejection.

In a broader embodiment the applicant's findings can be used to predict, diagnose, assess, or monitor any event in which GRN-SP or a GRN-SP fragment is released into the circulation.

In one embodiment of the cardiac methods of the invention the GRN-SP biomarker level is measured one or more times on samples (or sample derivatives) taken from a subject within about six hours, or about four hours, or about two hours, or about one hour, about 30 minutes, or within about 15 minutes of presentation with the disorder, or its occurrence. Single or multiple GRN-SP biomarker measurements within six hours, four hours, two hours, one hour, one-half hour, and one-quarter hour are included within the invention. GRN-SP biomarker measurements or additional GRN-SP biomarker measurements on samples subsequently taken or derived from a subject following six hours are also included.

In one embodiment, the methods of the invention are in vitro methods.

In one embodiment, the biological sample is blood, saliva, interstitial fluid, plasma, urine, serum or heart tissue. In one preferred embodiment, the sample is blood or plasma.

In one embodiment, the measuring step comprises detecting binding between the GRN-SP biomarker and a binding agent that selectively binds the GRN-SP biomarker. The measuring step in one embodiment comprises:

(a) binding the GRN-SP biomarker with a binding agent; and
(b) measuring the level of bound GRN-SP biomarker.

The binding agent in one embodiment is an antibody or antigen-binding fragment thereof. Most commonly, the antibody is a monoclonal, polyclonal, bispecific, chimeric or humanized antibody.

In one embodiment the antibody is a monoclonal antibody.

In another embodiment, the levels of a GRN-SP biomarker are measured using mass spectroscopy.

The GRN-SP biomarker which is bound or detected by the antibody is the full length human GRN-SP molecule (SEQ ID NO:15) or an antigenic variant or fragment thereof. In one embodiment, the fragment is at least four continguous amino acids in length. In another embodiment the fragment that is bound or detected is human GRN-SP (1-9) SEQ ID NO:17. The antibody may bind the N-terminus or the C-terminus of the GRN-SP or GRN-SP fragment.

Specific antigenic peptides which the binding agent selectively binds include human GRN-SP (1-9) (SEQ ID NO:17), or antigenic-binding fragments, or variants thereof.

Binding of the GRN-SP biomarker in one embodiment is measured using antibodies or antibody fragments that are immobilised on a solid phase.

Levels of the GRN-SP biomarker may usefully be measured with an assay selected from RIA, ELISA, fluoroimmunoassay, immunofluorometric assay, mass spectrometry and immunoradiometric assay.

Accordingly, the invention also provides an assay for a GRN-SP biomarker in a biological sample from a subject, the assay comprising detecting and measuring the level of the GRN-SP biomarker in the sample or sample derivative using any known methods.

The invention also provides an assay for a GRN-SP biomarker comprising:

(a) binding one or more GRN-SP biomarkers from a sample; and
(b) measuring the level of bound GRN-SP biomarker.

The GRN-SP biomarker may be bound using a GRN-SP biomarker-binding agent of the invention.

The invention also provides a GRN-SP biomarker assay for use in predicting, diagnosing, assessing or monitoring biological event or disorder in a subject.

In one embodiment, the assay is an in vitro assay.

The dysglycemia related methods of the invention may further comprise measuring the level of one or more non-GRN-SP/GRN-SP fragment markers of, for example, diabetes and comparing the levels against marker levels from a control wherein a deviation in the measured level from the control level of non-GRN-SP marker, together with a measured level of GRN-SP which deviates from, or is lower than the control level of GRN-SP is predictive or diagnostic of, for example, diabetes or can be used to monitor diabetes, for example.

Non-GHR-SP/GHR-SP fragment markers for diabetes may include glucose, insulin, lactate and triglyceride or fatty acid levels. Other markers include HbA 1C and fructoseamine.

The cardiac related methods of the invention may further comprise measuring the level of one or more non-GRN-SP or non-GRN-SP fragment markers of said ACD, or cardiac transplant rejection, or ACD/pulmonary disorder and comparing the levels against marker levels from a control, or reference value or value range, wherein a deviation in the measured level from the control or reference level of non-GRN-SP marker, together with a measured level of the GRN-SP biomarker which is higher than a control or reference of GRN-SP biomarker level, is predictive or diagnostic of the ACD, or can be used to assess or monitor said ACD (including cardiac transplant rejection) or ACD/pulmonary disorder.

Markers for use in the context of acute coronary syndrome include troponin, troponin T, troponin I, creatine kinase MB, myoglobin, BNP, NT-BNP, BNP-SP, BNP-SP fragments, ANP, ANP-SP, ANP-SP fragments, LDH, aspartate aminotransferase, heart specific fatty acid binding protein (H-FABP), ischemia modified albumin, endothelin, adrenomedullin and angiotensin H.

In another aspect, the present invention also provides a GRN-SP biomarker binding agent. In one embodiment, the GRN-SP biomarker binding agent of the invention binds or detects:

(a) GRN-SP (1-23) SEQ ID NO:15;
(b) GRN-SP (1-9) SEQ ID NO:17;
(c) an amino acid sequence encoded by a nucleotide sequence selected from SEQ ID NO: 16 or SEQ ID NO:18; or
(d) a variant or fragment of any one of (a) to (c).

The binding agent is useful in predicting, diagnosing, assessing, or monitoring a biological event or disorder which correlates with the release of a GRN-SP or GRN-SP fragment into the circulation. Such events or disorders include diabetes, glucose handling disorders, and acute cardiac disorders (ACD) in a subject.

In one embodiment, the binding agent is an anti-GRN-SP antibody or an anti-GRN-SP fragment antibody, or an antigen-binding fragment of either.

The invention also provides an anti-GRN-SP biomarker antibody or antigen-binding fragment thereof which binds:

(a) GRN-SP amino acid sequence 1-23 (SEQ ID NO:15);
(b) GRN-SP amino acid sequence 1-9 (SEQ ID NO:17);
(c) an amino acid sequence encoded by a nucleotide sequence selected from SEQ ID NO:16 or SEQ ID NO:18; or
(d) a variant or fragment of (a) or (c).

The antibody may be a monoclonal, polyclonal, bispecific, chimeric or humanized antibody or binding fragments or constructs of either.

The invention is also directed to the use of a GRN-SP biomarker binding agent in the manufacture of a GRN-SP biomarker assay for assessing a biological event or disorder in a subject, or to the use of a GRN-SP biomarker binding agent in the manufacture of a prognostic, assessment, diagnostic or monitoring tool for a biological event or disorder in a subject. In one embodiment, the event or disorder correlates with the release of GRN-SP and/or a GRN-SP fragment into the circulation including from a glucose handling disorder, diabetes, or an acute cardiac disorder (ACD).

The invention also relates to the use of an antibody or antigen-binding fragment of the invention in the manufacture of a prognostic, diagnostic, assessment or monitoring tool for assessing a biological event or disorder which correlates with the release of GRN-SP and/or a GRN-SP fragment into the circulation including a glucose handling disorder, diabetes, acute cardiac disorder (ACD), cardiac transplant rejection or an ACD/pulmonary disorder in a subject.

In one embodiment the prognostic, diagnostic or monitoring tool is calibrated to measure GRN-SP levels in the range of from about 0.1 to about 500 pmol/L, about 1 to about 300 pmol/L, about 10 to about 250 or about 20 to about 150 pmol/L.

In another aspect, the invention provides a kit for predicting, diagnosing or monitoring a biological event or disorder in a subject, the kit comprising a GRN-SP biomarker binding agent of the invention.

In one embodiment the kit is calibrated to measure GRN-SP biomarker levels in the range of about 0.1 to about 500 pmol/L, about 1 to about 300 pmol/L, about 10 to about 250 pmol/L or about 20 to about 150 pmol/L.

In one embodiment the kit also includes instructions for predicting, diagnosing, assessing, or monitoring a biological event or disorder including a glucose handling disorder, for example, diabetes, or an ACD in a subject, from the GRN-SP biomarker level measured in a sample or a derivative of a sample and comparing the measured level to a control or reference level. A measured GRN-SP biomarker level which deviates from the control or reference level is indicative of a biological event or disorder, such as, for example, ACD (including transplant rejection), a glucose handling disorder or diabetes. In one embodiment the sample is obtained within four hours of onset or clinical presentation.

In another aspect, the invention relates to a nucleic acid molecule encoding a GRN-SP fragment wherein said nucleic acid is selected from
(a) SEQ ID NO:18 or a variant or fragment thereof;
(b) a sequence which has at least 70%, 75%, 80%, 85%, 90%, 95% or 99% sequence identity to SEQ ID NO:18;
(c) a sequence of at least 10 nucleotides in length, capable of hybridising under stringent conditions to SEQ ID NO:18 or a variant or fragment thereof;
(d) a complement of any one of (a) to (c);
with the proviso that the sequence is not SEQ ID NO:16.

In one embodiment, the GRN-SP fragment encoded by the nucleic acid molecule is GRN-SP (1-9) (SEQ ID NO:17).

The invention also provides a genetic construct comprising a nucleic acid molecule of the invention. In one embodiment the genetic construct is an expression construct. Also provided by the invention is a vector comprising the genetic construct, a host cell comprising the genetic construct or vector, a polypeptide encoded by a nucleic acid molecule of the invention, an antibody which selectively binds a polypeptide of the invention, and a method for recombinantly producing a polypeptide of the invention.

Accordingly, in another aspect the invention provides an isolated GRN-SP biomarker or a variant or fragment thereof selected from:
(a) GRN-SP (1-9) (SEQ ID NO:17) or a variant or fragment thereof;
(b) an amino acid sequence having at least 70%, 75%, 80%, 85%, 90%, 95% or 99% amino acid sequence identity to the polypeptide of SEQ ID NO:17; and
(c) a GRN-SP polypeptide encoded by a nucleic acid molecule of the invention.

The invention also relates to the use of a polypeptide of the invention in the preparation of an anti-GRN-SP biomarker antibody.

One method for recombinantly producing a polypeptide of the invention comprises the steps of:
(a) culturing a host cell comprising a genetic construct of the invention capable of expressing a polypeptide of the invention;
(b) selecting cells expressing the polypeptide of the invention;
(c) separating the expressed polypeptide from the cells; and optionally
(d) purifying the expressed polypeptide.

In one embodiment, the method comprises a pre-step of transfecting the host cells with the construct.

BRIEF DESCRIPTION OF THE DRAWINGS

The invention will now be described with reference to the figures in the accompanying drawings in which

FIGURES

FIG. 1A is a bar graph showing circulating GRN-SP (1-9) biomarker concentrations in patients are derived from a cardiac source.

FIG. 1B is a bar graph showing circulating mature ghrelin is cleared by the heart.

Figure 2:
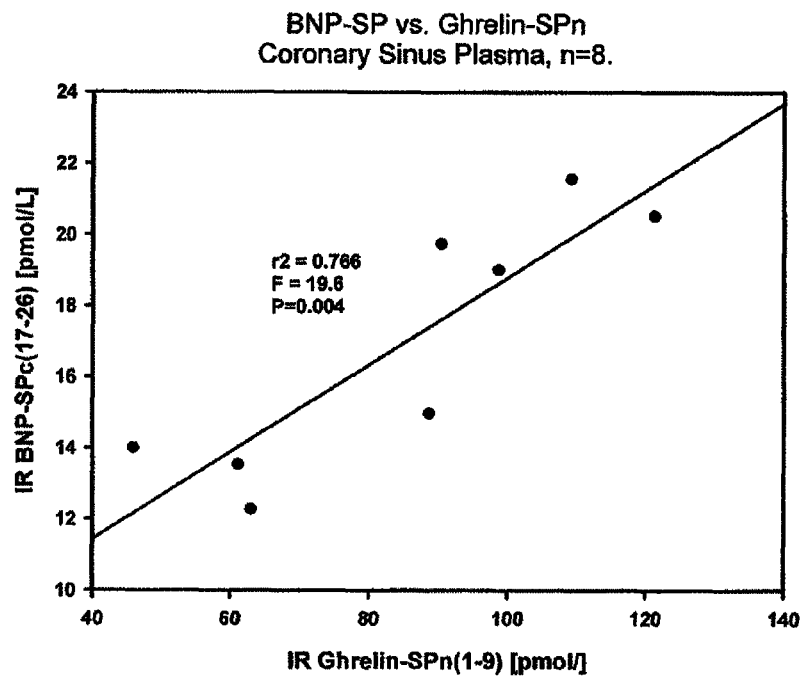

FIG. 2 shows the results of a radioimmunoassay demonstrating that plasma concentrations of GRN-SP (1-9) biomarker in healthy humans do not show any correlation with BMI.

Figure 3:
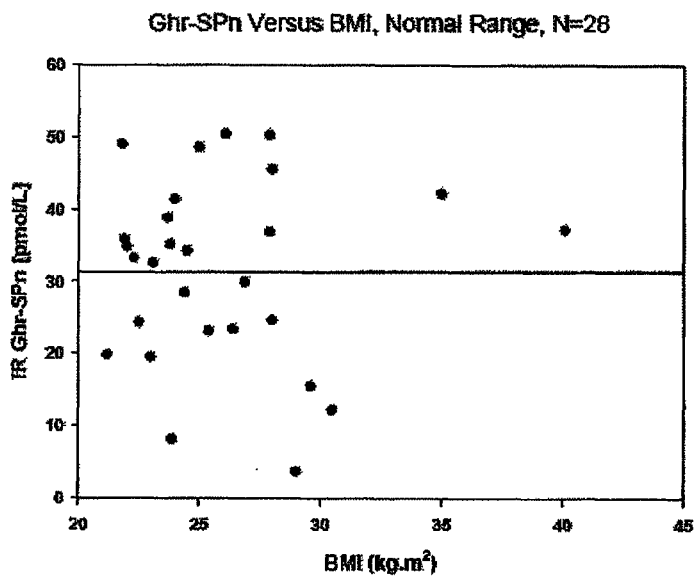

FIG. 3 shows the results of a radioimmunoassay demonstrating that Ghrelin-SPn(1-9) immunoreactivity in blood shows no correlation with body mass index in normal healthy individuals.

Figure 4:
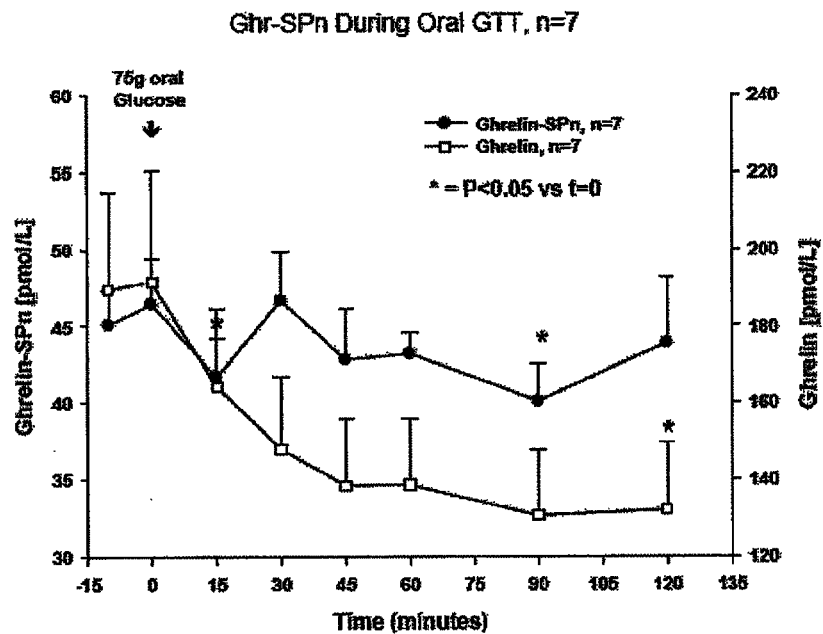

FIG. 4 shows the results of a radioimmunoassay demonstrating that immunoreactive plasma Ghrelin-SPn(1-9), like Gluelin itself, is significantly reduced by oral ingestion of 75 g glucose, a common test for insulin sensitivity and release under metabolic loading.

Figure 5:
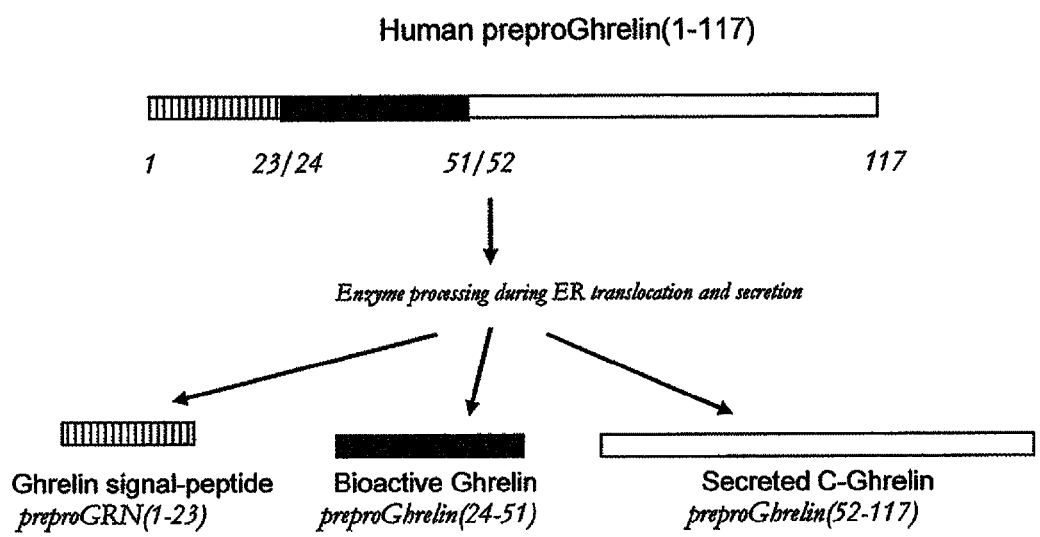

FIG. 5 is a schematic diagram outlining the processing of human preproGhrelin resulting in generation of free signal, N-ghrelin and ghrelin peptides.

Figure 6:
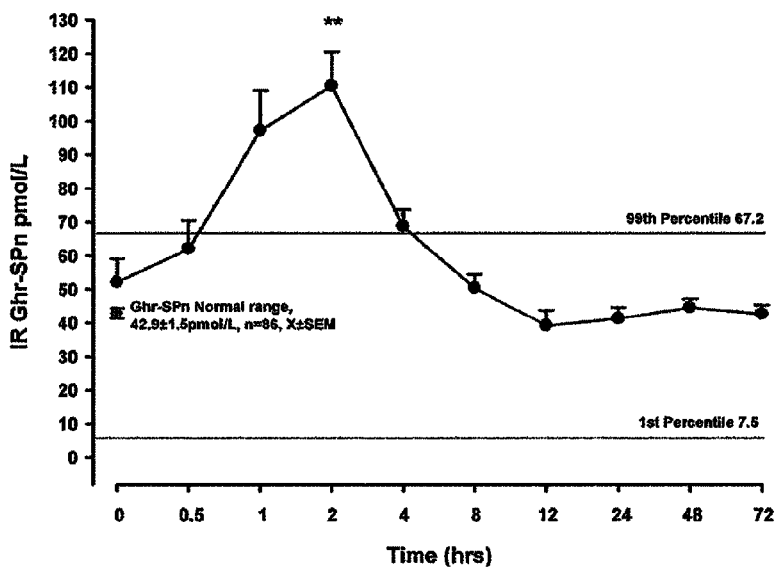
Figure 6:
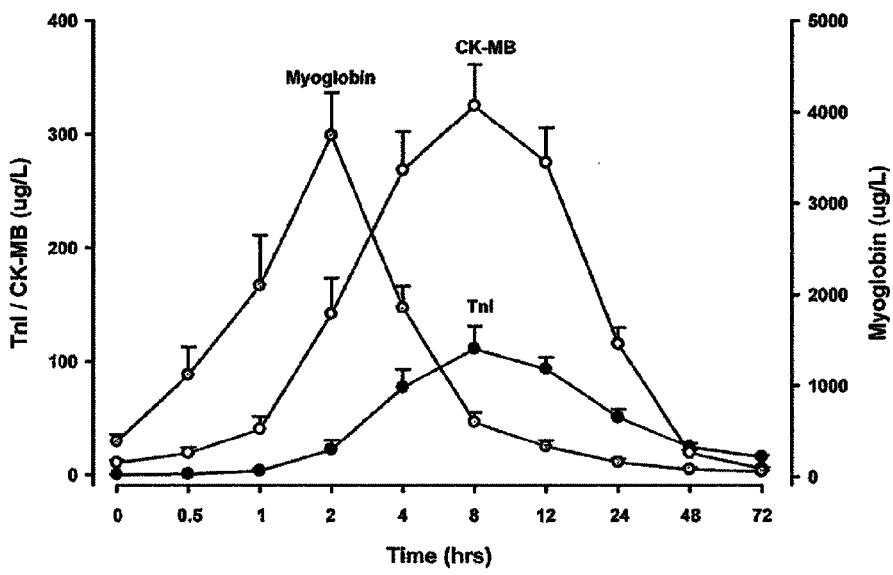

FIG. 6 Radioimmunoassay results showing Upper panel: Serial plasma concentrations of GHR-SPn (1-9) biomarker in patients with documented ST-elevation myocardial infarction (STEMI) from the time of presentation (t=0) at hospital emergency department. Note that peak levels of GHR-SPn were achieved about 1-2 hours after presentation and had returned to normal levels by 8-12 hours. Normal range data are indicated by the red lines showing upper and lower percentiles of the normal range. Lower panel: concomitant TnI, CK-MB and myoglobin plasma levels in the same STEMI patients identified in the upper panel.

FIG. 7 shows a table of cross reactivity data of GRN-SP (1-9) biomarker antiserum.

FIG. 8 shows a consensus alignment for ghrelin signal peptide sequences from rat, human, sheep, pig, mouse, dog and cat, respectively.

DEFINITIONS

Acute Cardiac Disorder (ACD), includes but is not limited to: acute coronary syndromes including acute myocardial infarction (AMI) with ST-elevation on presenting ECG, unstable angina, and acute non ST-elevated myocardial infarction; cardiac ischemia; acute cardiac injury; acute cardiac damage resulting from acute drug toxicity, acute cardiomyopathies, and cardiac transplant rejection. Full descriptive, definitions of these disorders are found in reference 1.

ACD/pulmonary disorder refers to a subject with an undiagnosed, or suspected ACD or pulmonary disorder.

Acute coronary syndromes (ACS) encompasses a wide spectrum of cardiac ischemia events including unstable angina, acute myocardial infarct with ST-elevation on presenting electrocardiogram (ECG), and acute myocardial infarction without ST-segment elevation on ECG.

The term "antibody" refers to an immunoglobulin molecule having a specific structure that interacts (binds) specifically with a molecule comprising the antigen used for synthesizing the antibody or with an antigen closely related to it. As used herein, the term "antibody" broadly includes full length antibodies and may also include certain antibody fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured. An antibody binds selectively or specifically to an GRN-SP polypeptide of the invention if the antibody binds preferentially to the GRN-SP e.g. has less than 25%, or less than 10%, or less than 1% or less than 0.1% cross-reactivity with a non-GRN-SP polypeptides. Usually, the antibody will have a binding affinity (dissociation constant (Kd) value), for the antigen or epitope of no more than $10^{-6}$, or $10^{-7}$M, or less than about $10^{-8}$M, or $10^{-9}$M, or $10^{-10}$, or $10^{-11}$ or $10^{-12}$M. Binding affinity may be assessed using surface plasma resonance, for example, or Scatchard analysis.

As used herein, an "antigen-binding fragment" or "antibody fragment" means a portion of the intact antibody that preferably retains most or all, or minimally at least one of the normal functions of that antibody fragment. Examples of antibody fragments include Fab, Fab', F(ab')$_2$ and Fv fragments, linear antibodies, diabodies, single chain antibodies (ScFV) and multispecific antibodies.

As used herein, a "monoclonal antibody" means an antibody that is a highly specific antibody directed against a single target antigen. A monoclonal antibody may be obtained from a population of homogenous or substantially homogenous antibodies wherein each monoclonal antibody is identical and/or bind the same epitope, except for natural mutations which may occur in minor amounts.

An "isolated antibody" is an identified antibody which has been separated or recovered, or both, from a component of its natural environment. For example, separated from proteins including enzymes and hormones. In one embodiment, the antibody is purified to at least 95%, or 96% or 97% or 98% or 99% by weight of antibody. Purity can be determined by the Lowry method for example. Ordinarily the antibody will be prepared by at least one purification step.

The term "binding agent" as used herein refers to any solid or non-solid material capable of binding GRN-SP or a fragment or variant thereof. In one embodiment the term refers to any natural or non-natural molecule that binds to GRN-SP or a fragment or variant thereof. Examples of binding agents include proteins, peptides, nucleic acids, carbohydrates, lipids, and small molecule compounds. A selective or specific binding agent is an antibody or antigen-binding fragment thereof.

Sample or biological sample as used herein means any sample taken or derived from a subject to be screened. The sample may be any sample known in the art in which the GRN-SP biomarker can be detected. Included are any body fluids such as plasma, blood, saliva, interstitial fluid, serum, urine, synovial, cerebrospinal, lymph, seminal, amniotic, pericardial fluid and ascites, as well as tissues such as cardiac tissues but not limited thereto.

The term "epitope" includes any protein determinant capable of specific binding to an immunoglobulin and/or T cell receptor. That is, a site on an antigen to which B and/or T cells respond. Epitopic determinants usually consist of chemically active surface groupings of molecules such as amino acids or sugar side chains, and usually have specific three dimensional structural characteristics, and specific charge characteristics. An epitope typically includes at least 3, 5 or usually 8-10 amino acids. The amino acids may be contiguous, or non-contiguous amino acids juxtaposed by tertiary folding.

The term "within six hours of onset or clinical presentation" includes from 1 minute up to and including 360 minutes from onset of, or presentation at a medical facility, for example, with ACD, cardiac transplant rejection or an undiagnosed or suspected ACD/pulmonary disorder. Measurements may be made within 4 hours (from 1 minute up to and including 240 minutes), within 2 hours (from 1 minute up to and including 120 minutes) or within 1 hour (from 1 minute up to and including 60 minutes) from onset or presentation, within 5 to 45 minutes, 15 to 40 minutes, 20 to 35 minutes, or within 25 to 30 minutes of onset or presentation.

A level "higher" or "lower" than a control or reference value, or a change, difference or deviation from a control or reference value, in one embodiment is statistically significant. A higher level, difference, lower level, deviation from, or change from a control level or reference value, or mean control level or reference value, can be considered to exist if the level differs from the control level or reference value, by about 5% or more, by about 10% or more, by about 20% or more, or by about 50% or more compared to the control level or reference value. Statistically significant may alternatively be calculated as $P \leq 0.05$. In a further alternative, higher levels, lower levels, deviation, and changes can be determined by recourse to assay reference limits or reference intervals. These can be calculated from intuitive assessment or non-parametric methods. Overall, these methods calculate the 0.025, and 0.975 fractiles as 0.025*(n+1) and 0.975 (n+1). Such methods are well known in the art.[22,23] Presence of a marker (including GRN-SP) absent in a control, is also contemplated as a higher level, deviation or change. Absence of a marker (including GRN-SP) present in a control, for example, is also contemplated as a lower level, deviation or change.

Included are samples taken or derived from any subjects such as from normal healthy subjects with no clinical history of biological events or disorders, including glucose handling disorders, diabetes or ACD, and subjects with various ACD's including but not limited to acute coronary syndromes: (AMI) with ST-elevation on presenting ECG, unstable angina, and acute non ST-elevated MI; cardiac ischemia; acute cardiac injury; acute cardiac damage resulting from acute drug toxicity, acute cardiomyopathies, and cardiac transplant rejection.

The term "cardiomyopathies" as used herein refers to diseases of the myocardium where the myocardium or heart muscle is weakened. This can result in reduced pumping of the heart. Common causes of cardiomyopathies are heart attacks, viral infections, high blood pressure, alcoholism, and autoimmune diseases.

A "biological event or disorder" as used herein refers to a range of events in which a GRN-SP biomarker is released into the circulation of a subject, including both acute and chronic conditions. Examplar conditions include metabolic disorders such as obesity, diabetes, kidney disease, a glucose handling disorder including metabolic syndrome, glucose intolerance, hyperglycaemia, and insulin resistance; non-alcoholic fatty liver disease (including non-alcoholic steatohepatitis) and fatty liver disease (including alcoholic liver disease); and cardiovascular disease (including ACD's such as, but not limited to acute coronary syndrome). Examples of chronic conditions are diabetes and cardiovascular disease.

The term GRN-SP refers to the complete 23 amino acid GRN signal peptide for the human preproghrelin sequence (SEQ ID NO: 1). GRN-SP (1-23) is shown separately in SEQ ID NO:15. GRN-SP biomarkers include GRN-SP, as well as GRN-SP-derived or GRN-SP-related polypeptides, comprising, consisting essentially of, or consisting of a variant or fragment of GRN-SP. Fragments useful as GRN-SP biomarkers include GRN-SP (1-9) (SEQ ID NO:17) In one embodiment GRN-SP functions as a signal polypeptide, or as an antigenic polypeptide to which an antibody can bind. Variants and fragments of GRN-SP include variants and fragments which retain at least the antigenic-binding functions.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "diabetes" as used herein encompasses both Type 1 (diabetes mellitus) and Type 2 diabetes. Type 1 diabetes is defined as a state of chronic hyperglycaemia. A venous plasma fasting glucose level of more than 7.0 mmol/L and/or a value exceeding 11.1 mmol/L either 2 hours after a glucose tolerance test, or in a random sample is indicative of type 1 diabetes (see Oxford Textbook of Medicine, Warrell et al; $4^{th}$ Ed, 2005, p 317).

The term "glucose handling disorder" as used herein includes various states of hyper- and hypoglycaemia (including metabolic syndrome). Hyperglycemic states include impaired glucose tolerance (IGT) and impaired fasting glucose (IFG). A venous plasma fasting glucose level of less than 7.0 mmol/L and glucose tolerance test value at 2 hours of between 7.8 and 11.1 mmol/L is indicative of IGT. Fasting glucose levels of 6.1 to 6.9 mmol/L is indicative of IFG (see Oxford Textbook of Medicine, Supra).

The term "glucose tolerance test" as used herein refers to the well known glucose test which commonly is administered after fasting by a subject drinking 75 g of anhydrous glucose dissolved in 250 ml of water (see Oxford Textbook of Medicine, Supra).

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to a nucleic acid molecule is to be similarly understood.

A "fragment" of a polynucleotide sequence provided herein is a subsequence of contiguous nucleotides that is capable of specific hybridization to a target of interest, e.g., a sequence that is at least 10 nucleotides in length. In one embodiment the fragments of the invention comprise at least 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68, contiguous nucleotides of a polynucleotide of SEQ ID NO:16. A fragment of a polynucleotide sequence can be used as a primer, a probe, included in a microarray, or used in polynucleotide-based selection methods herein. Fragments of other polynucleotides of the invention (such as SEQ ID NO:18) or polynucleotides described herein should be similarly understood. For example, for GRN-SP polynucleotide SEQ ID NO:18 a fragment has at least 10, 11, 12, 13, 15, 15, 16, 17, 18, 19, 20, 21, 22, 23, 24, 25 or 26 contiguous nucleotides of SEQ ID NO:18.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

The term "polypeptide", as used herein, encompasses amino acid chains of any length, including full length sequences in which amino acid residues are linked by covalent peptide bonds. Polypeptides useful in the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof. Polypeptides herein may have chain lengths of at least 4 amino acids, at least 5 amino acids, or at least 6, at least 7, at least 8, at least 9, at least 10, at least 11, at least 12, at least 13, at least 14, at least 15, at least 16, at least 17, at least 18, at least 19, at least 20, at least 21, at least 22, or all 23 amino acids of the full-length GRN-SP protein (SEQ ID NO:15). Reference to other polypeptides of the invention (such as SEQ ID NO:17) or other polypeptides described herein should be similarly understood.

A "fragment" of a polypeptide is a subsequence of the polypeptide that performs a function that is required for the biological activity or binding and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof. In one embodiment the fragment is capable of performing the above signal peptide activity, or retains the antigenic-binding properties of GRN-SP (1-23), GRN-SP (1-9), or other polypeptide of the invention or polypeptide described herein.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques. The polynucleotide or polypeptide sequences may be prepared by at least one purification step.

The term "purified" as used herein does not require absolute purity. Purified refers in one embodiment to at least 90%, or 95%, or 98%, or 99% homogeneity of a polynucleotide, polypeptide antibody, or host cell in a sample. The term should be similarly understood in relation to other molecules and constructs described herein.

The term "isolated" as applied to a cell or host cell describes a cell or host cell that has been obtained or removed from an organism or from its natural environment and is subsequently maintained in a laboratory environment as known in the art. The term is not limited to single cells, per se, but refers to a cell or host cell comprised in a cell culture and can include a single cell or single host cell.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

As used herein, the term "variant" refers to polynucleotide or polypeptide sequences different from the specifically identified sequences, wherein one to 18 or more nucleotides, and 1 to 6 or more or amino acid residues are deleted, substituted, or added. Substitutions of 1, 2, 3, 4, 5, 6, 7, 8, 9, 10, 11, 12, 13, 14, 15, 16, 17 or 18 nucleotides are specifically contemplated. Substitutions, additions or deletions of one, two, three, four, five or six amino acids are also contemplated. Variants may be naturally occurring allelic variants, or non-naturally occurring variants. Variants may be from the same or from other species and may encompass homologues, paralogues and orthologues. In certain embodiments, variants of the polypeptides useful in the invention have biological activities including signal peptide activity or antigenic-binding properties that are the same or similar to those of the parent polypeptides or polynucleotides. The term "variant" with reference to polynucleotides and polypeptides encompasses all forms of polynucleotides and polypeptides as defined herein.

Variant polynucleotide sequences exhibit at least 50%, at least 60%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a sequence of the present invention. Identity is found over a comparison window of at least 10 nucleotide positions, at least 15 nucleotide positions, at least 20 nucleotide positions, at least 27 nucleotide positions, at least 40 nucleotide positions, at least 50 nucleotide positions, at least 60, or at least 65 nucleotide positions or over the entire length of a polynucleotide of SEQ ID NO:16. For other polynucleotides disclosed herein identity may be similarly determined. For example, for SEQ ID NO:18 the comparison window may be over at least 10, 11, 12, 13, 14, 15, 16, 17, 18, 19, 20, 21, 22, 23, 24, 25, 26 or 27 nucleotide positions.

Polynucleotide sequence identity may be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment (Computer Applications in the Biosciences 10, 227-235).

Polynucleotide variants also encompass those which exhibit a similarity to one or more of the specifically identified sequences that is likely to preserve the functional equivalence of those sequences and which could not reasonably be expected to have occurred by random chance. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-5}$, less than $1\times10^{-6}$, less than $1\times10^{-9}$, less than $1\times10^{-12}$, less than $1\times10^{-15}$, less than $1\times10^{-18}$ or less than $1\times10^{-21}$ when compared with any one of the specifically identified sequences.

Polynucleotide sequence identity and similarity can also be determined in the following manner. The subject polynucleotide sequence is compared to a candidate polynucleotide sequence using sequence alignment algorithms and sequence similarity search tools such as in Genbank, EMBL, Swiss-PROT and other databases. Nucleic Acids Res 29:1-10 and 11-16, 2001 provides examples of online resources.

Use of BLASTN is preferred for use in the determination of sequence identity for polynucleotide variants according to the present invention.

BLASTN (from the BLAST suite of programs, version 2.2.18 Apr. 2008 in bl2seq (Tatiana A. et al, FEMS Microbiol Lett. 174:247-250 (1999), Altschul et al., Nuc. Acis Res 25:3389-3402, (1997)), is publicly available from NCBI (ftp://ftp.ncbi.nih.gov/blast/) or from NCBI at Bethesda, Md., USA. The default parameters of bl2seq are utilized except that filtering of low complexity parts should be turned off.

The identity of polynucleotide sequences may be examined using the following UNIX command line parameters:

bl2seq –i nucleotideseq1 –j nucleotideseq2 –F F –p blastn

The parameter –F F turns off filtering of low complexity sections. The parameter –p selects the appropriate algorithm for the pair of sequences. The bl2seq program reports sequence identity as both the number and percentage of identical nucleotides in a line "Identities=".

Alternatively, variant polynucleotides are polynucleotides that hybridize to the specified polynucleotide sequence, or a complement thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing, incorporated herein by reference). Tm for polynucleotide molecules greater than about 100 bases can be calculated by the formula Tm=81.5+0.41% (G+C-log(Na+) (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In one embodiment stringent conditions use 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulphate at 42° C., with washes at 42° C. in 0.2×SSC and 50% formamide at 55° C., followed by a wash comprising of 0.1×SSC containing EDTA at 55° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length) ° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the bl2seq program via the tblastx algorithm as described above.

The term "variant" with reference to polypeptides also encompasses naturally occurring, recombinantly and synthetically produced polypeptides. Variant polypeptide sequences preferably exhibit at least 50%, at least 60%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a sequence of the present invention. Identity is found over a comparison window of at least 5, at least 7, at least 10, at least 15, at least 20, at least 21, or at least 22 amino acid positions, or over the entire length of a polypeptide such as SEQ ID NO:15, or other polypeptides disclosed or used in the invention. For example, for SEQ ID NO:17 the comparison window may be over at least 5, 6, 7, 8 or amino acid positions, or over the entire length of the polypeptide.

Polypeptide variants also encompass those which exhibit a similarity to one or more of the specifically identified sequences that is likely to preserve the functional equivalence of those sequences and which could not reasonably be expected to have occurred by random chance. As discussed above, in the case of GRN-SP variants function may be as either a signal polypeptide, or antigenic polypeptide, or both.

Polypeptide sequence identity and similarity can be determined in the following manner. The subject polypeptide sequence is compared to a candidate polypeptide sequence using BLASTP (from the BLAST suite of programs, version 2.2.18 [Apr. 2008]]) in bl2seq, which is publicly available from NCBI (ftp://ftp.ncbi.nih.gov/blast/). The default parameters of bl2seq are utilized except that filtering of low complexity regions should be turned off.

The similarity of polypeptide sequences may be examined using the following UNIX command line parameters:

bl2seq -i peptideseq1-j peptideseq2-F F -p blastp

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Variant polypeptide sequences commonly exhibit an E value of less than $1\times10^{-5}$, less than $1\times10^6$, less than $1\times10^{-9}$, less than $1\times10^{-12}$, less than $1\times10^{-15}$, less than $1\times10^{-18}$ or less than $1\times10^{-21}$ when compared with any one of the specifically identified sequences.

Polypeptide sequence identity may also be calculated over the entire length of the overlap between a candidate and subject polypeptide sequences using global sequence alignment programs. EMBOSS-needle (available at http:/www.e-bi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

In one embodiment variants include peptides who's sequence differs from the human GRN-SP (1-23) SEQ ID NO:15, or GRN-SP (1-9) SEQ ID NO:17 herein by one, two, three, four, five, six or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine. Examples of conservative substations can also be found in the sequences of GRN-SP as shown in the sequence listings whereby the substitutions in different mammalian species compared to the human sequence are shown. Other conservative substitutions can be taken from FIG. 8 and Table 1 below.

TABLE 1

| Original Residue | Exemplary Substitutions | Other substitutions |
|---|---|---|
| Ala (A) | val; leu; ile | |
| Arg (R) | lys; gln; asn | |
| Asn (N) | gln; his; lys; arg | |
| Asp (D) | glu | |
| Cys (C) | ser | tyr |
| Gln (Q) | asn | |
| Glu (E) | asp | |
| Gly (G) | pro; ala | arg, ser |
| His (H) | asn; gln; lys; arg | |
| Ile (I) | leu; val; met; ala; phe; norleucine | |
| Leu (L) | norleucine; ile; val; met; ala; phe | |
| Lys (K) | arg; gln; asn | |
| Met (M) | leu; phe; ile | val |
| Phe (F) | leu; val; ile; ala; tyr | |
| Pro (P) | ala | val, leu, ser, thr |
| Ser (S) | thr | |
| Thr (T) | ser | ala |
| Trp (W) | tyr; phe | leu |
| Tyr (Y) | trp; phe; thr; ser | |
| Val (V) | ile; leu; met; phe; ala; norleucine | |

Naturally occurring residues are divided into groups based on common side-chain properties:
(1) hydrophobic: norleucine, met, ala, val, leu, ile;
(2) neutral hydrophilic: cys, ser, thr;
(3) acidic: asp, gin;
(4) basic: asn, gin, his, lys, arg:
(5) residues that influence chain orientation: gly, pro; and
(6) aromatic: trp, tyr, phe.

Non-conservative substitutions will entail exchanging a member of one of these classes for a member of another class.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

Substitutions, deletions, additions or insertions may be made by mutagenesis methods known in the art. A skilled worker will be aware of methods for making phenotypically silent amino acid substitutions. See for example Bowie et al., 1990, Science 247, 1306.[9], Kunkel, T; 1985, PNAS, 85 p 488.[27]

Also included within the polypeptides of the invention are those which have been modified during or after synthesis for example by biotinylation, benzylation, glycosylation, phosphorylation, amidation, by derivatization using blocking/protecting groups and the like. Such modifications may increase stability or activity of the polypeptide. Such modifications are well known in the art. See for example, Sambrook and Ausubel (supra), and Lundblad, R., CRC Press, 1995.[28]

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
(a) a promoter functional in the host cell into which the construct will be transformed,
(b) the polynucleotide to be expressed, and
(c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences and/or other regulatory elements.

"Regulatory elements" and "polynucleotide regulatory elements" mean any element that controls or influences the expression of a polynucleotide insert from a vector, genetic construct or expression cassette and includes promoters, transcription control sequences, translation control sequences, origins of replication, tissue-specific regulatory elements, temporal regulatory elements, enhancers, polyadenylation signals, repressors and terminators. Regulatory elements can be homologous or heterologous to the polynucleotide insert to be expressed from a vector, genetic construct or expression cassette according to the invention.

"Homologous" as used herein with reference to the relationship between a polynucleotide regulatory element (PRE) and the sequence to which the PRE is operably linked in a genetic construct means that the PRE is normally associated in nature with the coding sequence to which it is operably linked in the construct. A homologous polynucleotide regulatory element may be operably linked to a polynucleotide of interest such that the polynucleotide of interest can be expressed from a, vector, genetic construct or expression cassette according to the invention.

"Heterologous" as used herein with reference to the relationship between a polynucleotide regulatory element (PRE) and the sequence to which the PRE is operably linked in a genetic construct means that the PRE is not normally associated in nature with the coding sequence to which it is operably linked in the construct. Such PREs may include promoters normally associated with different genes (other than ANP), and/or promoters isolated from any other bacterial, viral, eukaryotic, or mammalian cell.

"Operably-linked" means that the sequence to be expressed is placed under the control of regulatory elements that include promoters, transcription control sequences, translation control sequences, origins of replication, tissue-specific regulatory elements, temporal regulatory elements, enhancers, polyadenylation signals, repressors and terminators.

The term "noncoding region" refers to untranslated sequences that are upstream of the translational start site and downstream of the translational stop site. These sequences are also referred to respectively as the 5' UTR and the 3' UTR.

These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

"Subject" as used herein is preferably a mammal and includes human, and non-human mammals such as cats, dogs, horses, cows, sheep, deer, mice, rats, primates (including gorillas, rhesus monkeys and chimpanzees), possums and other domestic farm or zoo animals. In one embodiment, the mammal is human.

The term "presentation" as used herein refers to presentation of a subject at a medical facility such as a clinic or hospital.

A "therapeutically effective amount" or "therapeutically effective dose" as used herein means an amount sufficient to produce the desired physiological effect or an amount capable of achieving the desired result, particularly for treating the desired disease or condition, including reducing or eliminating one or more symptoms or manifestations of the disease or condition.

The term "treat", "treating" or "treatment" and "preventing" refer to therapeutic or prophylactic measures which alleviate, ameliorate, manage, prevent, restrain, stop or reverse progression of a biological event characterized by an GRN-SP level which shows a deviation from normal control levels, including a glucose handling disorder, diabetes, hyperglycemia, obesity, cardiovascular disease, ACD, or cardiac transplant rejection or effects thereof, particularly of ACS. The subject may show observable or measurable (statistically significant) reduction in one or more of glucose, lactate, insulin, fatty acids, triglycerides Tn, TnI, TnT, BNP, N-BNP, BNP-SP (and fragments thereof), ANP, ANP-SP (and fragments thereof), creatine kinase-MB, myoglobin, LDH, aspartate aminotransferase, H-FABP, ischemia modified albumin, endothelin, adrenomedullin, renin, angiotensin II, and other usual clinical markers known to those skilled in the art, indicating improvement.

The term "mass spectrometry" as used herein refers to methods of filtering, detecting, and measuring ions based on their mass to charge ratio. See for example U.S. Pat. No. 5,719,060, U.S. Pat. No. 6,204,500, U.S. Pat. No. 6,107,623, U.S. Pat. No. 6,124,137, U.S. Pat. No. 6,225,047, U.S. Pat. No. 6,268,144, U.S. Pat. No. 7,057,165, and U.S. Pat. No. 7,045,366. Common mass spectrometry techniques include matrix-assisted laser desorption ionization (MALDI) and surface-enhanced laser desorption ionization (SELDI). Both may be coupled with time of flight analysers (MALDI-TOF and SELDI-TOF) which allow for analysis of analytes at femtomole levels in very short ion pulses.

Versions of SELDI discussed for example in U.S. Pat. No. 5,719,600, U.S. Pat. No. 6,124,137, and U.S. Pat. No. 6,225,047 which are useful in this invention include Surface-Enhanced Affinity Capture (SEAC), Surface-Enhanced Neat Desorption (SEND), and Surface-Enhanced Photolabile Attachment and Release (SEPAR).

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION OF THE INVENTION

Ghrelin (GRN) is a polypeptide hormone produced by the endocrine cells in the placenta, kidney, hypothalamus and pituitary. In the stomach (the main site of ghrelin production), epithelial cells lining the fundus produce ghrelin. Ghrelin is involved in the regulation of energy balance. Ghrelin acts to increase appetite, food consumption and ultimately body weight in an individual by activating hypothalamic feeding centers. Hyperglycemia is induced, and insulin release inhibited by ghrelin. Ghrelin and its receptor are also found in cardiovascular tissue (Garcia, E et al; Ghrelin and Cardiovascular health, Current Opinion in Pharmacology, vol 6, Issue 2, 2006, p 142-147). As SEQ ID NO:1 shows preproGRN is a 117 amino acid molecule. It consists of two polypeptide chains (A and B), linked by disulphide bridges. Preproghrelin (1-117) is cleaved to give a signal peptide of 23 amino acids (SEQ ID NO:15), proghrelin of 94 amino acids, and the ghrelin hormone of 28 amino acids. Processing of human preproghrelin is shown in FIG. 5.

It has long been thought that the functional role of the GRN-SP is limited to controlling the trafficking of ghrelin in the endoplasmic reticulum. Once this is achieved it has been assumed that the signal peptide is then degraded without ever being secreted from the cell.[25]

Confounding customary views, the present applicants have now found that GRN-SP typically in the form of GRN-SP fragments appears in the circulation. This finding itself means GRN-SP and GRN-SP fragments are useful as a circulating biomarker for a range of biological events or disorders. For example, it is anticipated that in diabetics and undiagnosed diabetics, for example, the level of GRN-SP will be above or below the normal control or reference level, depending on whether the subject is hypo- or hyper-insulinemic. The lower level is symptomatic of a deficiency in insulin action or secretion.

Accordingly, in one aspect, the invention provides a method for predicting, diagnosing or monitoring a biological event or disorder in a subject wherein the event or disorder correlates with the release of GRN-SP biomarker into the circulation, the method comprising:
  (a) measuring the level of GRN-SP biomarker in a biological sample from the subject; and (b) comparing the level of GRN-SP biomarker with the GRN-SP level from a control or reference level, wherein a deviation in the measured level from the control or reference level is indicative of a biological event or disorder.

The biological event or disorder includes glucose handling disorders, diabetes and ACD.

The invention therefore also provides a method for assessing glucose handling in a subject, the method comprising:

(a) measuring the level of GRN-SP biomarker in a subject after administration of glucose;

(b) comparing the level of said GRN-SP biomarker with the GRN-SP from a control or reference level, wherein a deviation in the measured level of GRN-SP from the control or reference level is indicative of a glucose handling disorder.

Commonly, the deviation will be a lower measured level of GRN-SP compared to a control level. For example, in a subject with hyperglycaemia.[31]

In this method, glucose may be administered as a first step, according to the well known glucose tolerance test protocol (Oxford Textbook of Medicine, Supra).

Assessments of plasma concentrations of GRN-SP biomarkers, usually venous plasma GRN-SP, may be made at 2 hours after the glucose test is administered in accordance with standard protocols. However, intermediate measurements for example at 15, 30, 45, 60, 90 and 105 minutes after administration of the glucose are also useful.

The invention also provides a method for predicting, diagnosing or monitoring diabetes, or diabetic potential in a subject, the method comprising:

(a) measuring the level of GRN-SP biomarker in a biological sample from the subject; and (b) comparing the level of GRN-SP biomarker with the GRN-SP level from a control or reference, wherein a measured level of GRN-SP biomarker higher or lower than the control or reference level is indicative of diabetes or a predisposition to diabetes.[31]

Whether the GRH-SP biomarker level is higher or lower than normal will depend on the insulin state of the subject.

The applicants have also surprisingly found that in patients with acute myocardial infarction (AMI) the circulating concentration of GRN-SP is highest in the first few hours following the onset of the patient's symptoms—in fact, at the time of presentation to the hospital or clinic. Levels observed in the first two to six hours, or four hours were surprisingly very high often reaching a peak some 1.5 to five, commonly two to three fold higher than levels in a normal control population. There has been no previous suggestion of the use of ghrelin or GRN-SP or GRN-SP fragments as a marker for ACD, cardiac transplant rejection or for use on undiagnosed or suspected ACD or pulmonary disorders.

These findings suggest GRN-SP biomarkers are useful as a very clear early stage marker of cardiac transplant rejection, ACD including acute coronary syndromes (ACS) such as AMI, particularly non-ST elevated MI, and acute cardiac ischemia, and may be used to distinguish ACD from pulmonary disorders.

Based on these surprising findings, the applicants have determined for the first time, that it would be useful to screen for circulating GRN-SP or variants or fragments thereof, as well as, or alternately nucleotide sequences encoding GRN-SP or the variants and fragments thereof in a biological sample taken from a subject, particularly within about six, about four or about two hours of onset of or at clinical presentation with the disorder.

Useful in the invention are antigenic fragments or variants of GRN-SP which are least 4 or 5 amino acids in length. Peptides having as few as 4 amino acids are known to be biologically active. See for example Gilchrist et al, Biology and Reproduction, 21, 732-739, 2004; and Sela et al., Behring Ins. Mitt, 91, 54-66, 1992. Particularly useful fragments are at the N-terminus (1-9) or C-terminus of GRN-SP. Examples of specific antigenic peptides are GRN-SP 1-9 (SEQ ID NO:17). The corresponding nucleotide sequence is given in SEQ ID NO:18. This sequence is provided by the applicants for the first time. Both the nucleic acid molecules and peptides form aspects of the invention.

Accordingly, in another aspect, the invention provides a nucleic acid molecule encoding a GRN-SP fragment wherein said nucleic acid is (a) SEQ ID NO:18 or a variant or fragment thereof;

(b) a sequence which has at least 70%, 75%, 80%, 85%, 90%, 95% or 99% sequence identity to SEQ ID NO:18;

(c) a sequence of at least 10 nucleotides in length, capable of hybridising under stringent conditions to SEQ ID NO:18 or a fragment or variant thereof;

(d) a complement of any one of (a) to (c);

with the proviso that the sequence is not SEQ ID NO:16. SEQ ID NO:16 is the full length nucleic acid sequence encoding the signal peptide.

The invention also provides isolated GRN-SP polypeptides and GRN-SP fragments encoded by a nucleic acid molecule of the invention.

Specific polypeptides of the invention include a polypeptide having the amino acid sequence of SEQ ID NO:17 as set forth in the accompanying sequence listing. Also contemplated are variants and fragments of these polypeptides as defined herein, or amino acid sequences having at least 70%, 75%, 80%, 85%, 90%, 95% or 99% amino acid identity to the polypeptide of SEQ ID NO:17. In one embodiment the variants or fragments are functionally equivalent variants or fragments. That is the variants or fragments maintain the function of SEQ ID NO:17 as antigens or signal peptides. The known full length GRN-SP (1-23) SEQ ID NO:15 is of course not claimed per se, but is useful in the present invention. For example, the polypeptides may be used in the preparation of anti-GRN-SP antibodies.

The nucleic acid molecules of the invention or otherwise described herein are in one embodiment isolated. They can be isolated from a biological sample using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser. The nucleic acid molecules of the invention can be amplified using primers, as defined herein, derived from the polynucleotide sequences of the invention. (See for example Mullis, Sambrook supra; and Molecular Diagnostic PCR Handbook Gerrit, V et al., Springer, 2005).

Further methods for isolating polynucleotides include use of all, or portions of, the polynucleotide of the invention, particularly a polynucleotide having the sequence set forth in SEQ ID NO:18 as hybridization probes. The technique of hybridizing labeled polynucleotide probes to polynucleotides immobilized on solid supports such as nitrocellulose filters or nylon membranes, can be used to screen genomic or cDNA libraries. Similarly, probes may be coupled to beads and hybridized to the target sequence. Isolation can be effected using known art protocols such as magnetic separation. Exemplary stringent hybridization and wash conditions are as given above.

Polynucleotide fragments may be produced by techniques well-known in the art such as restriction endonuclease digestion and oligonucleotide synthesis.

A partial polynucleotide sequence may be used as a probe, in methods well-known in the art to identify the corresponding full length polynucleotide sequence in a sample. Such methods include PCR-based methods, 5'RACE (Methods Enzymol. 218: 340-56 (1993); Sambrook et al., Supra) and hybridization-based method, computer/database-based methods. Detectable labels such as radioisotopes, fluorescent, chemiluminescent and bioluminescent labels may be used to facilitate detection. Inverse PCR also permits acquisition of unknown sequences, flanking the polynucleotide sequences disclosed herein, starting with primers based on a known region (Triglia et al., Nucleic Acids Res 16, 8186, (1998)) The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Supra). Primers and primer pairs which allow amplification of polynucleotides of the invention, also form a further aspect of this invention.

Variants (including orthologues) may be identified by the methods described. Variant polynucleotides may be identified using PCR-based methods (Mullis et al., Eds. 1994 The Polymerase Chain Reaction, Birkhauser). Typically, the polynucleotide sequence of a primer, useful to amplify variants of polynucleotide molecules by PCR, may be based on a sequence encoding a conserved region of the corresponding amino acid sequence.

Further methods for identifying variant polynucleotides include use of all, or portions of, the specified polynucleotides as hybridization probes to screen genomic or cDNA libraries as described above. Typically probes based on a sequence encoding a conserved region of the corresponding amino acid sequence may be used. Hybridisation conditions may also be less stringent than those used when screening for sequences identical to the probe.

The variant sequences, including both polynucleotide and polypeptide variants, may also be identified by the computer-based methods discussed above.

In addition, multiple sequence alignments of a group of related sequences can be carried out with CLUSTALW (Thompson, et al., Nucleic Acids Research, 22:4673-4680 (1994), http://www-jbbmc.u-strasbg.fr/BioInfo/ClutsalW/Top.html) or T-COFFEE (Cedric Notredame et al., J. Mol. Biol. 302: 205-217 (2000))) or PILEUP, which uses progressive, pairwise alignments. (Feng et al., J. Mol. Evol. 25, 351 (1987)).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch et al., Nucleic Acids Res. 22, 3583 (1994); Hofmann et al., Nucleic Acids Res. 27, 215 (1999)) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., Nucleic Acids Res. 30, 235 (2002)). Prosearch is a tool that can search SWISS-PROT and EMBL databases with a given sequence pattern or signature.

Proteins can be classified according to their sequence relatedness to other proteins in the same genome (paralogues) or a different genome (orthologues). Orthologous genes are genes that evolved by speciation from a common ancestral gene and normally retain the same function as they evolve. Paralogous genes are genes that are duplicated within a genome and genes may acquire new specificities or modified functions which may be related to the original one. Phylogenetic analysis methods are reviewed in Tatusov et al., Science 278, 631-637, 1997.

As noted above, the invention also relates to GRN-SP polypeptides encoded by the nucleic acid molecules of the invention, and includes variants and fragments of these polypeptides.

In addition to the computer/database methods described above, polypeptide variants may be identified by physical methods, for example by screening expression libraries using antibodies raised against polypeptides of the invention (Sambrook et al., Molecular Cloning: A Laboratory Manual, 2nd Ed. Cold Spring Harbor Press, 1987) by recombinant DNA techniques also described by Sambrook et al. or by identifying polypeptides from natural sources with the aid of such antibodies.

Polypeptides, including variant polypeptides, may be prepared using peptide synthesis methods well known in the art such as direct peptide synthesis using solid phase techniques (e.g. Merrifield, 1963, in J. Am. Chem. Soc. 85, 2149; Stewart et al., 1969, in Solid-Phase Peptide Synthesis, WH Freeman Co, San Francisco Calif.; Matteucci et al. J. Am. Chem. Soc. 103:3185-3191, 1981, and Atherton et al., in Solid Phase Peptide Synthesis: a practical approach, IRL press (1989)) or automated synthesis, for example using a Synthesiser from Applied Biosystems (California, USA).

Mutated forms of the polypeptides may also be produced using synthetic methods such as site-specific mutagenesis of the DNA encoding the amino acid sequence as described by Adelmen et al; DNA 2, 183 (1983). See also Protein Protocols Handbook; Walker, J. Humana Press 2002.

The polypeptides and variant polypeptides herein are in one embodiment isolated. They may be isolated or purified from natural sources using a variety of techniques that are well known in the art (e.g. Deutscher, 1990, Ed, Methods in Enzymology, Vol. 182, *Guide to Protein Purification*, and Protein Protocols Handbook, supra). Technologies include HPLC, ion-exchange chromatography, and immunochromatography but are not limited thereto.

Alternatively the polypeptides and variant polypeptides may be expressed recombinantly in suitable host cells and separated from the cells as discussed below. The polypeptides and variants have utility in generating antibodies, and generating ligands amongst other uses.

The genetic constructs described herein may comprise one or more of the disclosed polynucleotide sequences and/or polynucleotides encoding the disclosed polypeptides, of the invention and may be useful for transforming, for example, bacterial, fungal, insect, mammalian or plant organisms. The genetic constructs of the invention are intended to include expression constructs as herein defined. Included are vectors (such as pBR322, pUC18, pU19, Mp18, Mp19, ColE1, PCR1 and pKRC), phages (such as lambda gt10), and M13 plasmids (such as pBR322, pACYC184, pT127, RP4, p1J101, SV40 and BPV), cosmids, YACS, BACs shuttle vectors such as pSA3, PAT28 transposons (such as described in U.S. Pat. No. 5,792,294) and the like.

The constructs may conveniently include a selection gene or selectable marker. Typically an antibiotic resistance marker such as ampicillin, methotrexate, or tetracycline is used.

Promoters useful in the constructs include β-lactamase, alkaline phosphatase, tryptophan, and tac promoter systems which are all well known in the art. Yeast promoters include 3-phosphoglycerate kinase, enolase, hexokinase, pyruvate decarboxylase, glucokinase, and glyceraldehydrate-3-phosphanate dehydrogenase but are not limited thereto.

Enhancers may also be employed to act on the promoters to enhance transcription. Suitable enhancers for use herein include SV40 enhancer, cytomeglovirus early promoter enhancer, globin, albumin, insulin and the like.

For a general discussion of constructs, promoters, enhancers, and host cells, see Principles of Gene Manipulation and Genomics; Primrose, S et al., Blackwell Publishing 2006, Ed. 7., and From Genes to Genomes: Concepts and Applications of DNA Technology, Dale, J et al., Wiley-Interscience, 2007, Ed. 2.

Methods for producing and using genetic constructs and vectors are well known in the art and are described generally in Sambrook et al., (supra), and Ausubel et al., Current Protocols in Molecular Biology, Greene Publishing, 1987. Methods for transforming selected host cells with the vectors are also known, for example, the calcium chloride treatment described by Cohen, S N; PNAS 69, 2110, 1972.

Host cells comprising the genetic constructs and vectors described may be derived from prokaryotic or eukaryotic sources, for example yeast, bacteria, fungi, insect (eg baculovirus), animal, mammalian or plant organisms. In one embodiment the host cells are isolated host cells. Prokaryotes most commonly employed as host cells are strains of *E. coli*. Other prokaryotic hosts include *Pseudomonas, Bacillus, Serratia, Klebsiella, Streptomyces, Listeria, Saccharomyces, Salmonella* and *Mycobacteria* but are not limited thereto.

Eukaryotic cells for expression of recombinant protein include but are not limited to Vero cells, HeLa, CHO (Chinese Hamster ovary cells), 293, BHK cells, MDCK cells, and COS cells as well as prostate cancer cell lines such as PrEC, LNCaP, Du 145 and RWPE-2. The cells are available from ATCC, Virginia, USA.

Prokaryotic promoters compatible with expression of nucleic acid molecules of the invention include known art constitutive promoters (such as the int promoter of bacteriophage lambda and the bla promoter of the beta-lactamase gene sequence of pBR322) and regulatable promoters (such as lacZ, recA and gal). A ribosome binding site upstream of the coding sequence may also be required for expression.

Host cells comprising genetic constructs, such as expression constructs, are useful in methods for recombinant production of polypeptides. Such methods are well known in the art (see for example Sambrook et al. supra). The methods commonly involve the culture of host cells in an appropriate medium in conditions suitable for or conducive to, expression and selection of a polypeptide of the invention. Cells with a selectable marker may additionally be grown on medium appropriate for selection of host cells expressing a polypeptide of the invention. Transformed host cells expressing a polypeptide of the invention are selected and cultured under conditions suitable for expression of the polypeptide. The expressed recombinant polypeptide, may be separated and purified from the culture medium using methods well known in the art including ammonium sulfate precipitation, ion exchange chromatography, gel filtration, affinity chromatography, electrophoresis and the like (e.g. Deutscher, Ed, 1990, Methods in Enzymology, Vol 182, Guide to Protein Purification). Host cells may also be useful in methods for production of a product generated by an expressed polypeptide of the invention.

In another aspect, the present invention provides a method for predicting, diagnosing or monitoring an acute cardiac disorder (ACD) in a subject, the method comprising: measuring the level of a GRN-SP biomarker in a biological sample taken or derived from the subject and comparing the level of said GRN-SP with the GRN-SP biomarker level from a control, reference value, or reference range, wherein a measured level of GRN-SP biomarker higher than the control or reference level is indicative of ACD.

In another aspect the invention provides a method for monitoring a response to treatment of a an acute cardiac disorder (ACD) in a subject, the method comprising measuring the level of GRN-SP biomarker in a biological sample from the subject and comparing the level of said GRN-SP biomarker with the GRN-SP level from a control, reference, or reference range wherein a change in the measured level of GRN-SP biomarker from the control or reference level is indicative of a response to the treatment.

It is known in the art that BNP precursors such as proBNP27-102 proBNP27-47, can be used in predicting or diagnosing a cardiac transplant rejection episode and to distinguish between pulmonary and cardiovascular causes of dyspnea (shortness of breath). See US 2005/0244902. It is contemplated that GRN-SP can be used as an early marker of a cardiac transplant rejection episode based on cardiac tissue analysis, and to distinguish pulmonary from acute cardiac disorders.

Accordingly, the invention also provides a method for predicting, diagnosing or monitoring a cardiac transplant rejection episode in a subject, the method comprising measuring the level of GRN-SP biomarker in a biological sample from a subject after heart transplant and comparing the level of said GRN-SP biomarker with the GRN-SP level from a control, reference or reference range, wherein a measured level of GRN-SP biomarker higher than a control level or reference is indicative of transplant rejection.

The invention also provides a method of distinguishing between a pulmonary disorder and an acute cardiac disorder (ACD) in a subject, the method comprising measuring the level of a GRN-SP biomarker in a biological sample from the subject, and comparing the level of said GRN-SP biomarker with the GRN-SP biomarker level from a control, or reference or reference range, wherein a measured level of GRN-SP biomarker higher than the control or reference level is indicative of ACD.

In one embodiment, the invention provides a method for predicting, diagnosing or monitoring an acute cardiac disorder (ACD), cardiac transplant rejection, or ACD/pulmonary disorder in a subject, the method comprising measuring the level of a GRN-SP biomarker in a biological sample from the subject within the first about two hours of onset of, or clinical presentation with ACD, cardiac transplant rejection or ACD/pulmonary disorder.

A measured level of a GRN-SP biomarker is compared with the GRN-SP biomarker level from a control, reference or reference range, wherein a measured level of GRN-SP higher than the control or reference level is indicative of ACD or transplant rejection.

The skilled reader will appreciate that for evaluation purposes, the GRN-SP biomarker level will generally correlate with a reference value or range or a control value.

As used herein a control can be an individual or group from which GRN-SP biomarker samples are taken and a mean GRN-SP biomarker level determined. Usually, the individual or group will comprise normal healthy individuals or a group of individuals not known to be suffering from a biological event to be monitored, such as glucose handling disorders, diabetes, ACD (including cardiac transplant rejection), or ACD/pulmonary disorder. GRN-SP biomarker levels in most individuals are between 35-50 pmol/L, and the mean control level is about 43 pmol/L. Alternatively, the control level may be assessed based on a plurality of readings from previously tested individuals or groups.

Another example of a control level is a ratiometric measure between a GRN-SP biomarker and ghrelin levels in cardiac tissue or tissue from a diabetic, or obese individual or individual with a glucose handling disorder. The subject's GRN-SP biomarker level(s) can be compared to the mean GRN-SP biomarker level for that control population. The GRN-SP level in the cardiac tissue control population may be in the order of about 1.5 to 5, commonly about 2 to 3 or about 2.5 to 3 times (or more) higher than GRN-SP levels in the normal control population. The GRN-SP level in the diabetic or glucose handling disorder control population may be in the order of two fold higher or lower than the GRN-SP levels in the normal control population.[31]

Alternatively, the control may be one or more readings or the mean of such readings taken from the same subject at an earlier time. Ascertaining appropriate controls and control levels for particular methods is well known in the art.

It will be appreciated that the step of measuring GRN-SP biomarker levels in a sample may be a single measurement on a single sample, or repeated measurements on a number of samples depending on the biological event being studied. In the case of ACD, measurement may comprise, for example, 1 to 20 measurements of a GRN-SP biomarker, 1 to 10, 1 to 5, 1 to 3, 1 or 2, or 2 or 3 measurements, in samples taken or derived from a subject at different times. In one embodiment the measurements are on samples taken within about the first six, five, four, three, two hours, or within one hour of, onset of or clinical presentation with a disorder. Single, or repeated measurements outside the sample period above may also be taken to establish whether the GRN-SP biomarker level risen or has fallen compared to the normal control level, or cardiac tissue control level, or related reference levels or ranges.

In one embodiment, the method comprises measuring GRN-SP biomarker levels in 1 or 2 samples taken within about the first hour of onset or presentation, followed by measuring GRN-SP biomarker levels in 1 or 2 samples taken within about two to about four hours, or about two to about three hours of onset or presentation, or initial measurement of the GRN-SP level.

As noted above, GRN-SP levels measured within the first six, four or two hours of onset or presentation and can be 1.5 to 5 times higher are usually two to three times higher than GRN-SP biomarker levels measured in a normal control.

In another embodiment, a level of a GRN-SP biomarker in the sample in the range about 65 to about 250 pmol/L, about 65 to about 200 pmol/L, about 70 to about 150, or about 70 to about 130 pmol/L, is indicative of ACD, cardiac transplant rejection, or distinguishes ACD from a pulmonary disorder.

In the case of a biological event or disorder such as diabetes or glucose handling disorders, for example, measurement may comprise multiple calculations in conjunction with established clinical assessment, such as regularly used for insulin.

The biological sample as defined above can be any biological material in which a GRN-SP biomarker can be located or secreted. In one embodiment a biological sample is a circulatory biological sample, for example blood, serum or plasma. In one embodiment, the biological sample is cardiac tissue.

Nucleic Acid Assays

The presence of GRN-SP and its level of expression in the sample may be determined according to methods known in the art such as Southern Blotting, Northern Blotting, FISH or quantitative PCR to quantitate the transcription of mRNA [(Thomas, Proc. Nat, Acad. Sci. USA 77: 5201-5205 1980), (Jain K K, Med Device Technol. 2004 May; 15(4):14-7)], dot blotting, (DNA analysis) or in situ hybridization using an appropriately labelled probe, based on the sequences provided herein.

Accordingly, the invention also provides an assay for detecting the presence of a nucleic acid molecule of the invention, in a sample, the method comprising:
(a) contacting the sample with a polynucleotide probe which hybridises to the nucleic acid sequence under stringent hybridisation conditions; and
(b) detecting the presence of a hybridisation complex in the sample.

In one embodiment the nucleic acid molecule is SEQ ID NO:18 or a variant or fragment thereof.

In one embodiment the hybridisation probe is a labelled probe. Examples of labels include fluorescent, chemiluminescent, radioenzyme and biotin-avidin labels. Labelling and visualisation of labelled probes is carried out according to known art methods such as those above.

For convenience the nucleic acid probe may be immobilized on a solid support including resins (such as polyacrylamides), carbohydrates (such as sepharose), plastics (such as polycarbonate), and latex beads but not limited thereto.

As discussed above the nucleic acid molecule probe may preferably be an RNA, cDNA or DNA molecule. In one embodiment the probe is, or includes SEQ ID NO:18.

Stringent hybridisation conditions are as discussed above.

The expression level of the nucleic acid marker may be determined using known art techniques such as RT-PCR and electrophoresis techniques including SDS-PAGE. Using these techniques the DNA or cDNA sequence of a nucleic acid molecule of the invention, in a subject sample is amplified, and the level of DNA or cDNA or RNA measured.

In an alternate method the DNA, cDNA or RNA level may be measured directly in the sample without amplification.

In one embodiment the method is Northern blot hybridization analysis. Probes for use in Northern blot hybridization analysis may be prepared based on the GRN-SP biomarker sequences identified herein. In one embodiment, a probe includes at least 10, at least 12, 15, 18, 21, 24, 27, 30, 36, 42, 51, 60, 63, 66 or 69 or more contiguous nucleotides of a reference sequence.

Alternatively, the expression level may be measured using reverse transcription based PCR (RT-PCR) assays using primers specific for the nucleic acid sequences. If desired, comparison of the level of the GRN-SP biomarker polynucleotide in the sample can be made with reference to a control nucleic acid molecule the expression of which is independent of the parameter or condition being measured. A control nucleic acid molecule refers to a molecule in which the level does not differ between the disorder or transplant rejection state and the healthy state. Levels of the control molecule can be used to normalise levels in the compared populations. An example of such a control molecule is GAP-DH. The GRN-SP biomarker polynucleotides of the invention will change levels with the biological event or disorder.

Peptide Assays

In one embodiment the measuring step comprises detecting binding between a GRN-SP biomarker and a binding agent that binds, (including selectively or specifically binds) GRN-SP or a fragment or variant thereof. As a pre-step in the measurement a GRN-SP biomarker polypeptide may be bound with a binding agent that binds GRN-SP or a fragment or variant thereof.

Accordingly, in one embodiment the invention provides an assay for a GRN-SP biomarker in a biological sample, the assay comprising detecting and measuring the level of GRN-SP biomarker in the sample using any known methods.

In one embodiment, the biological sample is obtained from a subject within six or four hours from onset of ACD, cardiac transplant rejection, or ACD/pulmonary disorder or within six or four hours of clinical presentation with ACD, cardiac transplant rejection, or ACD/pulmonary disorder.

In one embodiment, the invention provides an assay for a GRN-SP biomarker comprising:
 (a) binding one or more GRN-SP biomarker polypeptides from a biological sample; and
 (b) measuring the level of bound GRN-SP biomarker polypeptide.

In one embodiment, the GRN-SP biomarker polypeptide is GRN-SP 1-9 (SEQ ID NO:17) or a variant or fragment thereof. It will be appreciated that in one embodiment more than one type of GRN-SP polypeptide may be bound in the assay, for example, GRN-SP 1-9 and GRN-SP 1-23.

In one embodiment, the GRN-SP biomarker polypeptide is bound using a binding agent. The binding agent may be a selective (specific) binding agent. That is, it has low cross-reactivity with other markers of biological events, and more particularly ghrelin. The binding agent in one embodiment is an antibody or antigen-binding fragment thereof. Where an antibody is used in the assay, the antibody may be raised against any antigenic part of the GRN-SP biomarker, including the N-terminal, or C-terminal. In one embodiment the antibody is raised against GRN-SP (1-23) SEQ ID NO:15; GRN-SP (1-9) SEQ ID NO:17 or an amino acid sequence encoded by a nucleotide sequence of the invention; or a variant or fragment thereof.

The present invention also relates to such binding agents, antibodies, and antigen-binding fragments of the antibodies and their uses. Uses include in an assay, or in the manufacture of an assay, prognostic, diagnostic or monitoring tool for GRN-SP. The assay or tool may be used to monitor a biological event or disorder in a subject including a glucose handling disorder, diabetes and ACD.

The antibodies may be in isolated or purified form. An antibody that binds to GRN-SP or a fragment or variant thereof may be in any form, including all classes of polyclonal, monoclonal, bispecific, single chain, human, humanized antibodies and chimeric antibodies produced by genetic recombination. Also included is antiserum obtained by immunizing an animal such as a mouse, rat or rabbit with GRN-SP or a fragment or variant thereof. The antibodies may bind to a common GRN-SP sequence in a group of GRN-SP fragments, or to a specific GRN-SP fragment, or even to sets of GRN-SP fragments.

A fragment of an antibody or a modified antibody may also be used herein so long as it binds GRN-SP or a fragment or variant thereof. The antigen-binding fragment may be Fab, F(ab'), F(ab'), an Fc or Fv fragment or single chain Fv (scFv), in which Fv fragments from H and L chains are ligated by an appropriate linker (Huston et al. Proc. Natl. Acad. Sci. USA 85:5879-83 (1988)). The "Fc" portion of an antibody refers to that portion of an immunoglobulin heavy chain that comprises one or more heavy chain constant region domains; CH1, CH2 and CH3, but does not include the heavy chain variable region.

The "Fv" portion of an antibody is the minimum antibody fragment that contains a complete antigen-recognition and antigen binding site. The region consists of a dimer of one heavy chain and one light chain variable domain in tight, non-covalent association.

Fab fragments contain the constant domain of the light chain and the first constant domain (CH1) of the heavy chains. Fab' fragments have a few residues added to the Fab carboxy terminus of the CHI domain including one or more cysteines from the antibody hinge region. F(ab')$_2$ fragments represent pairs of Fab' fragments with cysteine hinges between them, that have been separated. The F(ab')$_2$ fragment has two-antigen binding sites. Fab fragments may be produced by papain digestion of antibodies.

For a discussion of antibodies and fragments see for example PNAS USA 81: 6851-6855 (1984), Protein Eng 8(10) 1057-1062 (1995); The Pharmacology of Monoclonal Antibodies, vol. 113, Springer-verlag 1994, Rosenburg and Moore Eds; PNAS USA 90: 6444-6448 (1993); Nature 321: 522-525 (1986); Nature 332: 323-329 (1988), and WO 2005/003154.

Methods for preparing antibodies, and detecting, modifying and isolating same are well known in the art (see for example Maintaining and using Antibodies: A Practical Handbook, Howard, G et al., CRC Press 2006; Protein-protein Interactions: A Molecular Cloning Manual, Golemis E (Ed), CSHL Press, 2002; Harlow and Lane (1998,[11] Milstein[18], Suresh[19], and Brennan[29]) In one embodiment antibodies used are produced by immunizing a suitable host mammal. Fusion proteins comprising GRN-SP may also be used as immunogens.

An antibody may be modified by conjugation with a variety of molecules, such as polyethylene glycol (PEG), biotin, streptavidin, and chemiluminescent, fluorescent, calorimetric, and radioimmunometric labels as discussed herein. The modified antibody can be obtained by chemically modifying an antibody. These modification methods are conventional in the field.

Alternatively, an antibody may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared using known art methods.[16,17,22]

In brief, methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include GRN-SP or a fragment or variant thereof or a fusion protein thereof. It may be useful to conjugate the immunizing agent to a protein known to be immunogenic in the mammal being immunized. Examples of such immunogenic proteins include but are not limited to keyhole limpet hemocyanin, bovine serum albumin, bovine thyroglobulin, and soybean trypsin inhibitor. Examples of adjuvants which may be employed include Freund's complete adjuvant and MPL TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods well known in the art. See for example Kohler and Milstein, 1975[11], U.S. Pat. No. 4,196,265, U.S. Pat. No. 4,816,567 and Golemis (supra). The hybridoma cells may be cultured in a suitable culture medium, alternatively, the hybridoma cells may be grown in vivo as ascites in a mammal. Preferred immortalized cell lines are murine myeloma lines, which can be obtained, for example, from the American Type Culture Collection, Virginia, USA. Immunoassays may be used to screen for immortalized cell lines which secrete the antibody of interest. Sequences of GRN-SP or fragments or variants thereof may be used in screening.

Accordingly, also contemplated herein are hybridomas which are immortalized cell lines capable of secreting a GRN-SP specific monoclonal antibody.

Well known means for establishing binding specificity of monoclonal antibodies produced by the hybridoma cells include immunoprecipitation, radiolinked immunoassay (RIA), enzyme-linked immunoabsorbent assay (ELISA) and Western blot. (Lutz et al., Exp. Cell. Res. 175:109-124 (1988), Golemis (supra), and Howard (supra)). For example, the binding affinity of the monoclonal antibody can, for example, be determined by the Scatchard analysis described in Munson et al., Anal Biochem 107: 220 (1980). Samples from immunised animals may similarly be screened for the presence of polyclonal antibodies.

Monoclonal antibodies can also be obtained from recombinant host cells. DNA encoding the antibody can be obtained from a hybridoma cell line. The DNA is then placed into an expression vector, transfected into host cells (eg, COS cells, CHO cells, E. coli cells) and the antibody produced in the host cells. The antibody may then be isolated and/or purified using standard techniques.

Other known art techniques for monoclonal antibody production such as from phage libraries, may also be used. See for example, Nature 352: 624-628 (1991).

To facilitate detection, antibodies and fragments herein may be labelled with detectable markers such as fluorescent, bioluminescent, and chemiluminescent compounds, as well as radioisotopes, magnetic beads and affinity labels (e.g biotin and avidin). Examples of labels which permit indirect measurement of binding include enzymes where the substrate may provide for a coloured fluorescent product, suitable enzymes include horseradish peroxidase, alkaline phosphatase, malate dehydrogenase and the like. Fluorochromes (e.g Texas Red, fluorescein, phycobiliproteins, and phycoerythrin) can be used with a fluorescence activated cell sorter. Labelling techniques are well known in the art.

The monoclonal antibodies secreted by the cells may be isolated or purified from the culture medium or ascites fluid by conventional immunoglobulin purification procedures such as, for example, reverse phase HPLC, protein A-Sepharose, hydroxyapatite chromatography, gel electrophoresis, dialysis, or affinity chromatography. See for example, Scopes, Protein Purification: Principles and Practice, Springer-Verlag, NY (1982).

The monoclonal antibodies or fragments may also be produced by recombinant DNA means (see for example U.S. Pat. No. 4,816,567). DNA modifications such as substituting the coding sequence for human heavy and light chain constant domains in place of the homologous murine sequences (U.S. Pat. No. 4,816,567 above) are also possible. The antibodies may be monovalent antibodies. Methods for preparing monovalent antibodies are well known in the art (U.S. Pat. Nos. 5,334,708, 5,821,047, and 7,476,724). Production of chimeric (U.S. Pat. No. 4,816,567), bivalent antibodies (U.S. Pat. No. 5,843,708) and multivalent antibodies are also contemplated herein (U.S. Pat. No. 6,020,153).

Chimeric monoclonal antibodies are antibodies in which a portion of the heavy and/or light chain is identical with or homologous to corresponding sequences in antibodies derived from a particular species or belonging to a particular antibody (sub)class. The remainder of the chain is identical, or homologous to corresponding sequences in antibodies derived from another species or belonging to another antibody (sub)class, and fragments thereof, so long as they exhibit the requisite biological activity. (See U.S. Pat. No. 4,816,567 supra).

The antibodies of the invention may further comprise humanized antibodies or human antibodies. Humanized antibodies include human immunoglobulins in which residues from a complementary determining region (CDR) of the recipient are replaced by residues from a CDR of a non-human species. The production of humanized antibodies from non-human sources such as rabbit, rat and mouse are well known.[13,14,15]

Human antibodies can also be produced using various techniques known in the art, including phage display libraries[16]; and transgenic methods, see, for example Neuberger 1996[17]; and Vaughan et al, 1998[18].

Bispecific antibodies may also be useful. These antibodies are monoclonal, preferably human or humanized, antibodies that have binding specificities for at least two different antigens. For example GRN-SP or a variant or fragment thereof, and an antigen selected from the group including preproghrelin, ANP, ANP-SP, CK-MB, TnT, TnI, BNP, BNP-SP, NT-BNP, myoglobin, LDH, aspartate aminotransferase, H-FABP, ischemia modified albumin, endothelin, adrenomedullin, rennin and angiotensin II. Antibodies with greater than two specificities for example trispecific antibodies are also contemplated herein.

Methods for making bispecific antibodies are known in the art. See for example Milstein and Cuello 1983[19], Suresh et al., 1986[20] and Brennan et al., 1985.[21]

The GRN-SP biomarker which is bound or selectively bound by the antibody is GRN-SP or a variant or fragment thereof as discussed above.

In one embodiment, the antibody binds the N-terminus (1-9) of GRN-SP. An example of a specific antigenic peptides which the binding agent selectively binds includes GRN-SP (1-9) (SEQ ID NO:17).

Binding of a GRN-SP biomarker can be detected by any means known in the art including specific (antibody based) and non specific (such as HPLC solid phase). Most commonly, antibodies herein are detected using an assay such as ELISA or RIA as noted above. Competitive binding assays, sandwich assays, non-competitive assays, fluoroimmunoassay, immunofluorometric assay, or immunoradiometric assays, luminescence assays, chemiluminescence assays and mass spectrometry analysis such a surface-enhanced laser desorption and ionization (SELDI) electrospray ionization (ESI), matrix assisted laser-desorption ionization (MALDI), fourier transform Ion cyclotron resonance mass spectroscopy (FTICR) alone or in combination with non-specific binding agents such as chromatography formats are also feasible. See for example, Golemis, E and Howard G. (supra).

Conveniently, an antibody can be fixed to a solid substrate to facilitate washing and isolation of the GRN-SP/antibody complex. Binding of antibodies to a solid support can be achieved using known art techniques. See for example Handbook of Experimental Immunology, 4th edition, Blackwell Scientific Publications, Oxford (1986). Useful solid substrates for antibodies include glass, nylon, paper and plastics.

Similarly, GRN-SP can be adsorbed onto a solid substrate such as adsorbent silica, or resin particles, or silicon chips optionally coated or derivatised with ion exchange, reverse phase (eg C18 coating) or other materials. The substrate may be in the form of beads, plates, tubes, sticks or biochips. Examples of biochips include Ciphergen, ProteinChip arrays (Ciphergen Biosystems (CA, USA)), and Packard BioChips available from Perkin Elmer, USA. See also U.S. Pat. No. 6,225,047, U.S. Pat. No. 6,329,209. The biochips may include a chromatographic surface. Biochips or plates with addressable locations and discreet microtitre plates are particularly useful. Also preferred for use are multiplex systems where beads containing antibodies directed to multiple analytes are used to measure levels of the analytes in a single sample. Analytes to be measured may include other cardiac markers as well as GRN-SP or variants or fragments thereof. One example of a suitable multiplex bead system for use herein is the Luminex Fluorokine Multianalyte Profiling system.

Antibody assay methods are well known in the art see for example U.S. Pat. No. 5,221,685, U.S. Pat. No. 5,310,687, U.S. Pat. No. 5,480,792, U.S. Pat. No. 5,525,524, U.S. Pat. No. 5,679,526, U.S. Pat. No. 5,824,799, U.S. Pat. No. 5,851,776, U.S. Pat. No. 5,885,527, U.S. Pat. No. 5,922,615, U.S. Pat. No. 5,939,272, U.S. Pat. No. 5,647,124, U.S. Pat. No. 5,985,579, U.S. Pat. No. 6,019,944, U.S. Pat. No. 6,113,855, U.S. Pat. No. 6,143,576 and for unlabelled assays U.S. Pat. No. 5,955,377, and U.S. Pat. No. 5,631,171 see also Zola, Monoclonal Antibodies: A Manual of Techniques pp 147-158 (CRC Press, Inc 1987), Harlow and Lane (1998) Antibodies, A Laboratory Manual, Cold Spring Harbour Publications, New York, and US 2005/0064511 for a description of assay formats and conditions. All of the above references are incorporated herein by reference in their entirety.

Immunoassay analysers are also well known and include Beckman Access, Abbott AxSym, Roche ElecSys and Dade Behring Status systems amongst others which are well described[22].

Binding of a GRN-SP biomarker and an antibody to form a complex can be detected directly or indirectly. Direct detection is carried out using labels such as fluorescence, luminescence, radionuclides, metals, dyes and the like. Indirect detection includes binding detectable labels such as digoxin or enzymes such as horseradish peroxidase and alkaline phosphatase to form a labelled antibody followed by a step of detecting the label by addition of detection reagents.

Horseradish peroxidase for example can be incubated with substrates such as o-Phenylenediamine Dihydrochloride (OPD) and peroxide to generate a coloured product whose absorbance can be measured, or with luminol and peroxide to give chemiluminescent light which can be measured in a luminometer as is known in the art. Biotin or digoxin can be reacted with binding agents that bind strongly to them. For example, the proteins avidin and streptavidin will bind strongly to biotin. A further measurable label is then covalently bound or linked thereto either by direct reaction with the protein, or through the use of commonly available crosslinking agents such as MCS and carbodiimide, or by addition of chelating agents.

Generally, the complex is separated from the uncomplexed reagents for example by centrifugation. If the antibody is labelled, the amount of complex will be reflected by the amount of label detected. Alternatively, a GRN-SP biomarker may be labelled by binding to an antibody and detected in a competitive assay by measuring a reduction in bound labelled GRN-SP biomarker when the antibody-labelled-GRN-SP biomarker is incubated with a biological sample containing unlabelled GRN-SP biomarker. Other immunoassays may be used for example a sandwich assay.

In one embodiment, following contact with the antibody, usually overnight for 18 to 25 hours at 4° C., or for 1 to 2 to 4 hours at 25° C. to 40° C., the labelled GRN-SP biomarker bound to the binding agent (antibody) is separated from the unbound labelled GRN-SP biomarker. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between GRN-SP in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays have greater specificity, speed and greater measuring range. In this type of assay an excess of the primary antibody to a GRN-SP biomarker is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to the GRN-SP biomarker is also incubated with the sample either simultaneously or sequentially with the primary antibody. This second antibody is chosen to bind to a site on a GRN-SP biomarker that is different from the binding site of the primary antibody. These two antibody reactions result in a sandwich with the GRN-SP biomarker from the sample sandwiched between the two antibodies. The second antibody is usually labelled with a readily measurable compound as detailed above for competitive binding assays. Alternatively a labelled third antibody which binds specifically to the second antibody may be contacted with the sample. After washing away the unbound material the bound labelled antibody can be measured and quantified by methods outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

As discussed in the following examples, in one embodiment radioimmunoassay (RIA) is the laboratory technique used. In one RIA a radiolabelled antigen and unlabelled antigen are employed in competitive binding with an antibody. Common radiolabels include $^{125}$I, $^{131}$I, $^{3}$H and $^{14}$C.

Radioimmunoassays involving precipitation of a GRN-SP biomarker with a specific antibody and radiolabelled antibody binding protein can measure the amount of labelled antibody in the precipitate as proportional to the amount of the GRN-SP biomarker in the sample. Alternatively, a labelled GRN-SP biomarker is produced and an unlabelled antibody binding protein is used. A biological sample to be tested is then added. The decrease in counts from the labelled GRN-SP biomarker is proportional to the amount of GRN-SP biomarker in the sample.

In RIA it is also feasible to separate bound GRN-SP biomarkers from free GRN-SP biomarkers. This may involve precipitating the GRN-SP biomarker/antibody complex with a second antibody. For example, if the GRN-SP biomarker/antibody complex contains rabbit antibody then donkey anti-rabbit antibody can be used to precipitate the complex and the amount of label counted. For example in an LKB, Gamma-master counter. See Hunt et al.[22]

The methods of the invention further comprise measuring the levels of one or more other markers of glucose handling disorders, diabetes, kidney disease, cardiovascular disease, ACD, cardiac transplant rejection, or ACD/pulmonary disorder that are not a GRN-SP biomarker. The level of the other marker or markers can be compared to mean control levels from a control population. A deviation in the measured level from the mean control level is predictive or diagnostic of diabetes or a predisposition thereto, cardiovascular disease, ACD or cardiac transplant rejection.

The methods of the invention have been described with respect to a different, deviated or lower level or decrease in GRN-SP biomarker levels being indicative of glucose handling disorders or diabetes, and higher levels or increase in GRN-SP biomarker levels being indicative of ACD, or cardiac transplant rejection. It is also possible that in some events or disorders the levels of GRN-SP biomarkers will fall or be lower or will rise or be higher depending on the metabolic effect of the event or disorder. Measuring deviations above or below a control level are also contemplated.

Other markers which are particularly useful herein for ACD and cardiac transplant rejection include troponin, troponin T, troponin I, creatin kinase MB, myoglobin, BNP, NT-BNP, BNP-SP, BNP-SP fragments, ANP, ANP-SP, ANP-SP fragments, LDH, aspartate aminotransferase, H-FABP, endothelin, adrenomedullin, ischemia modified albumin, renin and angiotensin II[1]. These markers are all implicated in cardiac dysfunction or disease. For diabetes and glucose handling disorders, other markers include insulin, lactate, glucose, fatty acids and triglycerides or markers therefor. Assays for such markers are well known and used in the art. For example, various such assays are used routinely in clinical settings as described by Vogel, H, (2007) Drug Discovery and Evaluation: Pharmacological Assays Ed 3. Springer pp. Ed.: 3, pp 2071 and by Runge et al. (2006) Principles of Molecular medicine Ed. 2 Springer, pp 1268. Kits and reagents for performing such assays are commercially available from a number of suppliers including QuantiChrom™ and Enzy-Chrome™ glucose, fatty acid and triglyceride assays (Bio-Assay Systems, California, USA) and Glucose, Triglyceride and Free Fatty Acid Assay Kits (BioVision, California, USA).

Correlating the level of GRN-SP biomarker with other markers can increase the predictive, diagnostic or monitoring value of GRN-SP biomarkers. In the case of ACD, cardiac transplant rejection or ACD/pulmonary disorder combining GRN-SP biomarker levels with known cardiac markers can increase the predictive or diagnostic value of a patient outcome.

Analysis of a number of peptide markers can be carried out simultaneously or separately using a single test sample. Simultaneous, two or multi-site format assays are preferred. Multiplex bead, microassay or biochip systems are particularly useful. The beads, assays or chips can have a number of discreet, often addressable locations, comprising an antibody to one or more markers including GRN-SP and GRN-SP fragments. The one or more markers include more than one GRN-SP biomarker. For example, it may be useful to assay for N-terminal and C-terminal GRN-SP biomarker fragments and combine the assay results. Many other such marker combinations are feasible. US2005/0064511, U.S. Pat. No. 6,019, 944, and Ng and Hang, J. Cell Mol. Med., 6:329-340 (2002) provide a description of microarray, chips, capillary devices and techniques useful in the present invention. Luminex provides a multiplex bead system useful in the present invention. See also The Protein Protocols Handbook, supra. Laboratory analysers suitable for use with separate or sequential assays include AxSym (Abbott, USA), ElecSys (Roche), Access (Beckman), ADVIA CENTAUR® (Bayer) and Nichols Advantage® (Nichols Institute) immunoassay system.

In one embodiment simultaneous assays of a plurality of polypeptides are performed on a single surface such as a chip or array.

In another embodiment separate assays of one or more non-GRN-SP markers are performed and the results collated or combined with GRN-SP biomarker results.

Where a subject is to be monitored, a number of biological samples may be taken over time. Serial sampling allows changes in marker levels, particularly GRN-SP biomarkers to be measured over time. Sampling can provide information on the approximate onset time of an event, the severity of the event, indicate which therapeutic regimes may be appropriate, response to therapeutic regimes employed, or long term prognosis. Analysis may be carried out at points of care such as in ambulances, doctors offices, on clinical presentation, during hospital stays, in outpatients, or during routine health screening.

The methods of the invention may also be performed in conjunction with an analysis of one or more risk factors such as but not limited to age, weight, level of physical activity, sex and family history of events such as obesity, diabetes, glucose handling disorders, and cardiac events. Test results can also be used in conjunction with the methods of the invention. For example, glucose tolerance tests, ECG results and clinical examination. A statistically significant change in circulating level of GRN-SP, together with one or more additional risk factors or test results may be used to more accurately diagnose, prognose or monitor the subject's condition.

The methods herein can also be used as a guide to therapy. For example what therapies to initiate and when, therapy monitoring, detection of positive or adverse effects of therapy, for example heart toxicity of antimitotic drugs, insulin, glucose handling, triglyceride, and fatty acid concentrations, and adjustment of therapeutic regimes if and when required dependent on results. This can improve short, medium and long term outcomes for patients. For a guide to treatments see Troughton et al.[8]

Acute Cardiac Disorders

The applicants have shown that concentrations of GRN-SP biomarkers are correlated with acute cardiac disorders (FIG. 6). Moreover, GRN-SP biomarker levels are at their highest upon clinical presentation in the case of patients presenting with suspected acute myocardial infarction (AMI) or heart attack. Patients presenting with acute cardiac disorders, and in particular acute cardiac ischemia coronary artery disease caused by (heart attack leaving scarring in the heart muscle or myocardium) may or may not experience subsequent myocardial infarction (MI). The group which does not experience MI can not be readily diagnosed using current clinical techniques and markers. The applicants have therefore provided a useful early and specific marker for myocardial damage associated with MI. This may allow the early diagnosis of myocardial damage due to adverse events (AEs) and allow a physician to distinguish such cases from other acute coronary syndromes as well as from other causes of a chest pain. For example, angina, gastro-intestinal disease, lung/pleural disorders and the like. This significantly shortens the window of 6 hours to 12 hours currently experienced waiting for elevation of levels of current cardiac biomarkers such as myoglobin, CK-MB, TnT and TnI. A more precise diagnosis and treatment can therefore be effected earlier, reducing morbidity and mortality and giving better prognostic outcomes.

In another embodiment, the invention has application in monitoring reperfusion treatment in cardiac patients. Reperfusion treatment commonly includes percutaneous coronary intervention (eg angioplasty) and/or pharmacological treatment. Thrombolytic drugs for revascularisation are commonly employed in pharmacological treatment. Adjunctive therapies include anticoagulant and anti-platelet therapies. Reperfusion treatment is most effective when employed as soon as possible after diagnosis. GRN-SP testing to accelerate diagnosis allows prompt introduction of reperfusion treatment. Effectiveness of treatment can also be monitored by repeat testing, and therapy adjusted as appropriate. For a comprehensive discussion of reperfusion treatment see Braunwald et al herein.[1]

Cardiac Disease

The methods of the invention may also be useful to diagnose or predict cardiac disease in a subject.

Cardiac Transplant Rejection

The invention also has applications in monitoring heart transplant, commonly a cardiac allograft transplant, rejection through regular tissue biopsy during and after transplant using GRN-SP biomarker measurements. An increase in GRN-SP biomarker levels measured within about six, four or two hours, of heart transplant relative to a control level may be predictive or diagnostic of a rejection episode.

The present invention also provides an assay for GRN-SP biomarkers in a biological sample. In one embodiment the sample is obtained from a subject within about six, four or two hours from onset of, or within about six, four or two hours of clinical presentation with ACD, cardiac transplant rejection or ACD/pulmonary disorder. The assay comprises detecting and measuring the level of GRN-SP biomarker in the sample using any known methods. In one embodiment, the assay is an in vitro assay. Such methods include all of the known assay techniques discussed above as well as gel electrophoresis techniques, Western blot, gas phase spectroscopy, atomic force microscopy, surface plasmon resonance, mass spectroscopy but not limited thereto[23].

In one embodiment the assay comprises one or more nucleic acid sequences which bind to one or more of the GRN-SP biomarker nucleic acid sequences of the invention. A large range of sense and antisense probes and primers can be designed from the nucleic acid sequences herein. The expression level of the GRN-SP biomarker sequence is identified using known art techniques discussed above. The array can be a solid substrate e.g., a "chip" as described in U.S. Pat. No. 5,744,305 or a nitrocellulose membrane. For a discussion of useful arrays see for example Microarray Technology and its Application, Müller, U et al., Springer 2005, and Gene Expression Profiling by Microarrays: Clinical Implications, Hofmann, W-K; Cambridge University Press 2006.

Proteins expressed by the GRN-SP biomarker herein may also be used in assays, and results compared to expression levels of the same protein expressed in a normal control sample. Protein presence and quantity may be assessed using assay formats known in the art and discussed herein.

The presence of GRN-SP biomarker is preferably detected in the sample by binding GRN-SP biomarker to a binding agent such as an antibody, including an antibody of the invention and measuring the presence of the amount of bound GRN-SP biomarker.

As noted above, antibodies which bind or selectively bind GRN-SP including variants and fragments thereof, form a further aspect of the invention and the antibodies may be prepared by the techniques discussed above. The antibodies are useful in the methods and assays of the invention.

In a further aspect, the invention provides a kit for predicting, diagnosing, assessing, or monitoring a biological event or disorder in a subject including glucose handling disorders, diabetes, cardiovascular disease, acute cardiac disorder (ACD, including cardiac transplant rejection), or ACD/pulmonary disorder, comprising an GRN-SP biomarker binding agent (or binding agents for multiple GRN-SP biomarkers) including an antibody or antigen-binding fragment of the invention. When the kit is for use in diagnosing ACD, cardiac transplant rejection, or an ACD/pulmonary disorder, the biological sample is in one embodiment, for example, obtained from a subject within about six, four or two hours of onset of, or clinical presentation with ACD, cardiac transplant rejection, or ACD/pulmonary disorder.

The invention also provides a kit for predicting, assessing, diagnosing or monitoring an acute cardiac disorder (ACD), cardiac transplant rejection, or an ACD/pulmonary disorder comprising a binding agent of the invention, wherein the kit is calibrated to measure GRN-SP levels in the range of about 0.1 to about 500 pmol/L, about 1 to about 300 pmol/L, about 10 to about 250 or about 20 to about 150 pmol/L.

Calibration of assays can be effected according to known art techniques, for example using blood samples with known levels of GRN-SP biomarker, or a set of calibrates with different known levels of GRN-SP in each. Test strips for use in diagnostic kits are commonly calibrated during manufacture. See for example U.S. Pat. No. 6,780,645. The kit is useful for measuring the level of GRN-SP biomarker in a biological sample. The detection reagents may be oligonucleotide sequences complementary to GRN-SP or a fragment of the GRN-SP marker, or antibodies which bind to the polypeptides encoded by the marker. The reagents may be bound to a solid matrix as discussed above or packaged with reagents for binding them to the matrix. The solid matrix or substrate may be in the form of beads, plates, tubes, dip sticks, strips or biochips all as discussed above.

Detection reagents include wash reagents and reagents capable of detecting bound antibodies (such as labelled secondary antibodies), or reagents capable of reacting with the labelled antibody.

The kit will also conveniently include a control reagent (positive and/or negative) and/or a means for detecting the nucleic acid, polypeptide or antibody. Instructions for use may also be included with the kit, such as taking a biological sample from a subject within six, four or two hours of onset or presentation with ACD, cardiac transplant rejection or ACD/pulmonary disorder, measuring the level of GRN-SP in the sample, comparing same to a control level and associating the result with cardiac status. Generally an increase in the GRN-SP marker level from a control is indicative of obesity, ACD or cardiac transplant rejection, or ACD as opposed to a pulmonary disorder.

In the case of diabetes a higher or lower GRN-SP biomarker level from a control is indicative of diabetes or a predisposition to same, whether it is higher or lower depending on the nature of the diabetes and the diabetic status of the subject.

Most usually, the kits will be formatted for assays known in the art, and in one embodiment for PCR, Northern hybridization or Southern ELISA assays, as are known in the art.

The kits may also include one or more additional assays for markers for ACD, transplant rejection, or ACD/pulmonary disorders. In the case of ACS the additional marker assay may include an assay or assays for one or more of troponin T, troponin I, creatin kinase MB, myoglobin, ANP, BNP, BNP-SP, BNP-SP fragments, ANP, ANP-SP, ANP-SP fragments, NT-BNP, LDH, aspartate aminotransferase, H-FABP, endothelin, adrenomedullin, ischemia modified albumin, renin and angiotensin II. In one embodiment all of the markers are included in the kit.

In the case of diabetes the additional kit components may be measurement means for markers that may include glucose, insulin, lactate and triglyceride or fatty acid levels or markers therefore.

The kit will be comprised of one or more containers and may also include collection equipment, for example, bottles, bags (such as intravenous fluids bags), vials, syringes, and test tubes. At least one container holds a product which is effective for predicting, diagnosing, or monitoring a biological event such as obesity, diabetes, kidney diseases, cardiovascular disease, ACD (particularly ACS), transplant rejection, or ACD/pulmonary disorder. The product is usually a nucleic acid molecule, polypeptide or a binding agent, particularly an antibody or antigen-binding fragment of the invention, or a composition comprising any of these. In a preferred embodiment, an instruction or label on, or associated with, the container indicates that the composition is used for predicting, diagnosing, or monitoring the biological event. Other components may include needles, diluents and buffers. Usefully, the kit may include at least one container comprising a buffer, such as phosphate-buffered saline, Ringer's solution and dextrose solution.

Binding agents that bind or selectively bind a GRN-SP biomarker (and optionally a non_GRN-SP biomarker) are desirably included in the kit. In one embodiment, the binding agent is an antibody, preferably an antibody or antigen-binding fragment of the invention. The antibody used in the assays and kits may be in one embodiment monoclonal or polyclonal and may be prepared in any mammal as discussed above. The antibodies may be prepared against a native peptide encoded or indicated by a GRN-SP biomarker nucleic acid sequence of the invention, GRN-SP (1-23), GRN-SP (1-9), or a synthetic peptide based on, or including same, or may be raised against an exogenous sequence fused to a nucleic acid sequence encoding an GRN-SP biomarker peptide of the invention.

In one kit embodiment a GRN-SP biomarker detection reagent is immobilized on a solid matrix such as a porous strip or chip to form at least one GRN-SP biomarker detection site. The measurement or detection region of the porous strip may include a plurality of detection sites, such detection sites containing a GRN-SP biomarker detection reagent. The sites may be arranged in a bar, cross or dot or other arrangement. A test strip or chip may also contain sites for negative and/or positive controls. The control sites may alternatively be on a different strip or chip. The different detection sites may contain different amounts of immobilized nucleic acids or antibodies eg, a higher amount in the first detection site and lower amounts in subsequent sites. Upon the addition of a test biological sample the number of sites displaying a detectable signal provides a quantitative or semi-quantitative indication of the amount of GRN-SP biomarker present in the sample.

Also included in the kit may be a device for sample analysis comprising a disposable testing cartridge with appropriate components (markers, antibodies and reagents) to carry out sample testing. The device will conveniently include a testing zone and test result window. Immunochromatographic cartridges are examples of such devices. See for example U.S. Pat. No. 6,399,398; U.S. Pat. No. 6,235,241 and U.S. Pat. No. 5,504,013.

Alternatively, the device may be an electronic device which allows input, storage and evaluation of levels of the measured marker against control levels and other marker levels. US 2006/0234315 provides examples of such devices. Also useful in the invention are Ciphergen's Protein Chip® which can be used to process SELDI results using Ciphergen's Protein Chip® software package.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

Example 1

Methods

All human protocols were approved by the Upper South Regional Ethics Committee of the Ministry of Health, New Zealand and were performed in accord with the Declaration of Helsinki.

Chemicals

Synthetic human GRN signal peptide GRN-SP(1-9), (SEQ ID NO:17) was synthesised by Mimotopes (Australia) using a mild Fmoc Solid Phase Synthesis method.[30] All buffer reagents were purchased from BDH® (UK) and/or Sigma (Mo, USA). GRN-SP(1-9) was synthesised with the C-terminal extended with cysteine for directional carrier coupling. GRN-SP(1-9) was also C-terminally extended with a tyrosyl residue for tracer preparation on the same peptide.

Human Studies

For the healthy volunteer reference range study, blood samples were initially obtained from 28 healthy volunteers (16 woman, average age 50.3±2.5 years (range 21-72 years), BMI 26.0±0.8 kg/m$^2$) after an overnight fast. The study was extended to a total of 86 volunteers. Samples were taken into tubes on ice and centrifuged at +4° C. at 2700 g for 5 min and the plasma stored at −80° C. until analysed.

The study was subsequently extended to 23 STEMI patients. Presenting at the Coronary Care Unit at Christchurch Hospital. After an overnight fast an 18-gauge intravenous cannula was inserted into a forearm vein for blood sampling. Venous samples (10 ml) were drawn on admission to the Coronary Care Unit (time 0) and thereafter at 00.5, 1, 2, 4, 8, 12, 24 and 72 hours as in patients, samples were taken into tubes on ice and centrifuged at +4° C. at 2700 g for 5 min and the plasma stored at −80° C. until analysed.

Plasma Extraction

All plasma samples were extracted on SepPak Cartridges, (Waters, USA) as previously described[22], dried and stored at −20° C. prior to RIA and HPLC.

Hormone Concentration Analysis

Plasma samples were assayed for Tn1, CK-MB and myoglobin using heterologous immunoassays on an Elecsys 2010 (Roche, USA) using ruthenium labelled biotinylated antibodies according to standard manufacturers protocols, Roche Diagnostics[17].

GRN-SP was measured by specific RIA as follows:

GRN-SP RIA

For the measurement of putative human GRN-SP biomarker peptides, we generated a novel RIA directed against GRH-SP amino acids 1-9 (SEQ ID NO:17) of the human preproghrelin(1-23) signal sequence (SEQ ID NO:15)

Antibody Generation preproGRN(1-9)$^{Cys10}$ was coupled to malemide treated N-e-maleimidocaproyloxy succinimide ester (EMCS) derivatised BSA in PBS (pH 7.0) by gentle mixing at room temperature. Coupled peptide was emulsified with Freund's (2 ml) adjuvant and injected subcutaneously (2 ml total) in 2 New Zealand white rabbits over 4-5 sites at monthly intervals. Rabbits were bled 12 days after injection to assess antibody titres until adequate levels were achieved. For RIA, GRN-SP IR was determined using antiserum at a final dilution of 1:15,000. This antiserum had no detectable cross reactivity with peptides and drugs indicated in FIG. 7 including human proBNP (1-13), proBNP (1-76), proANP (1-30), insulin, angiotensin II, angiotensin (1-7), urotensin II, CNP, ghrelin, C-ghrelin (52-117), proCNP (1-15), adrenomedulin, urocortin I, urocortin II, BNP-SPn(1-10), ANP-SPc (16-25), ANP-SP (1-10), INS-SPn (1-9). Cross reactivity was assessed following Klee, G G. Interference in hormone immunoassays Clin Lab Bed, 2004, 24:1-18.

Iodination and Assay Method preproGRN(1-9)$^{Tyr10}$ was iodinated via the Chloramine T method and purified on reverse phase HPLC (RP-HPLC) as previously described[21]. From this preparation an iodinated tracer form after RP-HPLC was tested. All samples, standards, radioactive traces and antiserum solutions were diluted in potassium based assay buffer.[22] The assay incubate consisted of 100 µL sample or standard (0-640 pmol human preproGRN(1-9) combined with 100 µL antiserum which was vortexed and incubated at 4° C. for 24 hours. 100 µL of trace (4000-5000 cpm) was then added and further incubated for 24 hours at 4° C. Free and bound immunoreactivities were finally separated by solid phase second antibody method (donkey anti-sheep Sac-Cel®, IDS Ltd, England) and counted in a Gammamaster counter (LKB, Uppsala, Sweden Statistical Analysis All results are presented as mean±SEM. Time-course data were analysed using two-way ANOVA for repeated measurements followed by least significant difference post-hoc testing. Correlation analysis of plasma hormone concentrations was carried out using a general linear regression model. In all analyses, a P-value<0.05 was considered significant.

Results

To determine if the 23 amino acid signal peptide of ghrelin, or fragments derived from it, are present in circulation of humans, we developed a specific radioimmunoassay (RIA) directed against residues 1-9 of preproghrelin(1-23). Dilution of plasma extracts demonstrate parallelism with the standard curve (not shown). Plasma concentrations of GRN-SP (1-9) in healthy humans were initially determined as 31.3±2.4 pmol/L (n=28). A subsequent larger study (n=86) gave plasma concentrations of 42.9±1.5 pmol/L (See FIG. 6). In healthy humans, concentrations of GRN-SP IR in blood do not show a significant correlation with BMI (FIG. 3).

Having established that immunoreactive (IR) GRN-SP biomarker (1-9) peptides are present in human plasma we then measured serial concentrations of IR GRN-SP (1-9) in patients with documented AMI (FIG. 6). Highest concentrations of IR GRN-SP were observed 1-2 hours after hospital admission and slowly dropped to stable levels over 72 hours. Importantly, average peak levels were 2 to 3 fold higher (range two to 5 fold higher) than levels in normal healthy volunteers. Peak concentrations of myoglobin occurred 1-2 hours after hospital admission, whereas peak TnI and CK-MB levels were not attained until 8-12 hours after admission.

Preferably, IR GRN-SP are detected.

To assess the role that GRN-SP may have in the control of metabolism and/or energy balance, 7 normal healthy volunteers were given 75 g oral glucose. As can be seen in FIG. 4, plasma levels of GRN-SP (1-9) and Ghrelin itself were significantly decreased after ingestion of glucose, consistent with it having a role in energy balance.

Example 2

Figure 1:
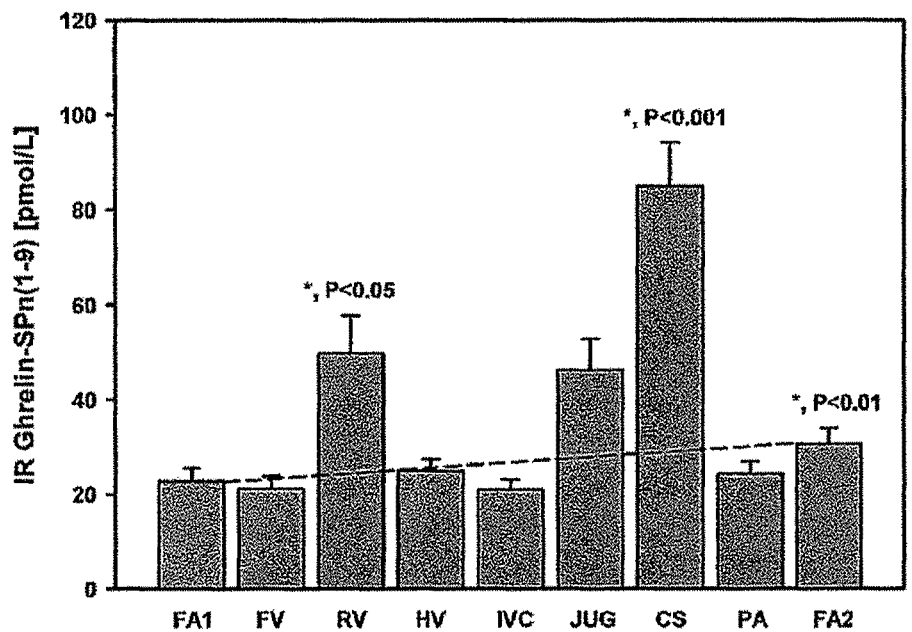
Figure 1:
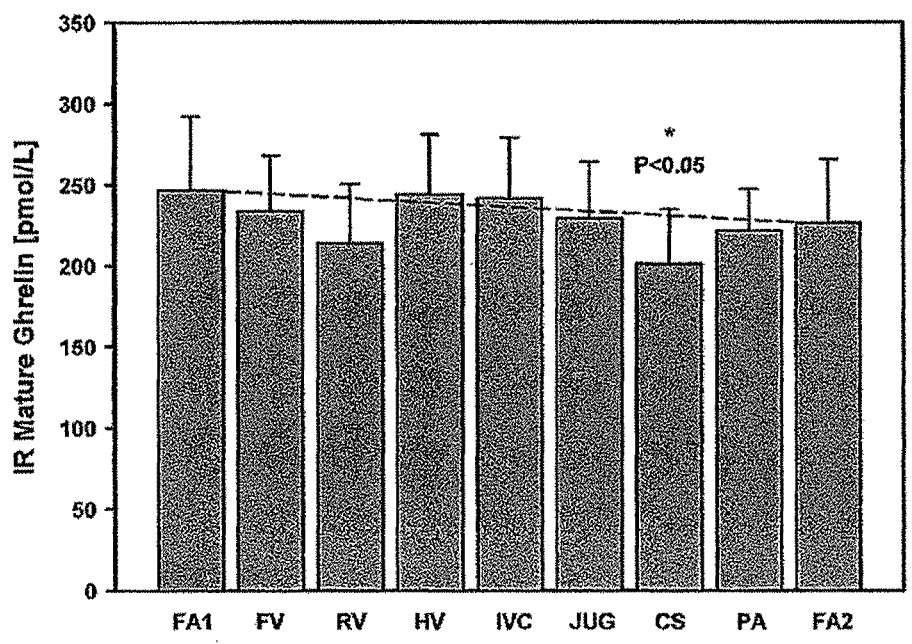

Eight patients with clinically stable suspected ACS were catheterized and blood samples from multiple organ sites: these were the femoral artery FA(1) and FA(2) femoral vein (FV), renal vein (RV), hepatic vein (HV), inferior vena cava (IVC), jugular (JUG), cardiac coronary sinus vein (CS) and pulmonary artery (PA). Blood was collected into chilled EDTA tubes, prepared from plasma by centrifugation and the plasma submitted to GRN-SP RIA. FIG. 1 clearly shows that the highest site of GRN-SP (1-9) concentration is the CS, the vein draining the heart, especially the ventricles. This is strong evidence that the heart is the predominant site of GRN-SP secretion. Consistent with this, coronary sinus levels of GRN-SP correlate strongly with another known cardiac peptide BNP-SP (FIG. 2).

Conclusion

Circulating GRN-SP biomarker concentrations in clinically stable patients are likely derived from cardiac sources. The significant cardiac secretion, is consistent with GRN-SP peptides and subpeptides being a cardiac hormone. The increase in GRN-SP peptides and subpeptides in response to documented AMI support the idea that they have a role as a biomarker of cardiac diseases. Furthermore, the response of GRN-SP biomarker plasma levels to increases in plasma glucose also suggests it may have a role in energy balance.

Discussion

This evidence is the first to document the signal peptide of preproghrelin and fragments thereof as being present in the circulation and extracellular space within two hours of a patient presenting with ACD or within two hours of the onset of ACD. We show in the first instance that the measurement of GRN-SP IR in blood has potential as a rapid biomarker of acute cardiac ischemia and/or subsequent injury and in the second instance, that measurement of GRN-SP IR after the event has potential merit as a marker of long term prognosis and outcome.

We also show that measurement in plasma of a GRN-SP biomarker has potential use in the arena of metabolism and/or energy balance, especially in the assessment of glucose handling.

Those skilled in the art will of course appreciate that the above description is provided by way of example and that the invention is not limited thereto.

REFERENCES

1. Braunwald E, Zipes D P, Libby P. Acute myocardial infarction Chp. 35 Heart disease: a textbook of cardiovascular medicine, 6$^{th}$ ed. 2001. pgs. 1114-1231.
2. Richards A M, Nicholls M G, Yandle T G, Frampton C, Espiner E A, Turner J G, Buttimore R C, Lainchbury J G, Elliott J M, Ikram H, Crozier I G, Smyth D W. Plasma N-terminal pro-brain natriuretic peptide and adrenomedullin: new neurohormonal predictors of left ventricular function and prognosis after myocardial infarction. Circulation 1998 97:1921-1929.
3. Jernberg T, Stridsberg M, Venge P, Lindahl B. N-terminal pro Brain Natriuretic Peptide on admission for early risk stratification of patients with chest pain and no ST-segment elevation. J. Am. Coll. Cardiology 2002 40:437-445.
4. Omland T, Persson A, Ng L, O'Brien R, Karlsson T, Herlitz J, Hartford M, Caidahl K. N-terminal pro-B-type natriuretic peptide and long-term mortality in acute coronary syndromes. Circulation. 2002 106:2913-2918.
5. Pemberton C J, Johnson M L, Yandle T G, Espiner E A. Deconvolution Analysis of the Secretion and Elimination of Cardiac Natriuretic Peptides During Acute Volume Overload. Hypertension 2000; 36: 355-359.
6. Richards A M, Nicholls M G, Troughton R W, Lainchbury J G, Elliott J, Frampton C, Espiner E A, Crozier J O, Yandle T G, Turner J. Antecedent hypertension and heart failure after myocardial infarction. J. Am. Coll. Cardiology. 2002 39: 1182-1188.
7. Troughton R W, Prior D L, Pereira J J, Martin M, Fogarty A, Morehead A, Yandle T G, Richards A M, Starling R C, Young J B, Thomas J D, Klein A L. Plasma B-type natriuretic peptide levels in systolic heart failure: importance of left ventricular diastolic function and right ventricular systolic function. J Am Coll Cardiol. 2004 43:416-422.
8. Troughton R W, Frampton C M, Yandle T G, Espiner E A, Nicholls M G, Richards A M. Treatment of heart failure guided by plasma amino-terminal brain natriuretic peptide (N-BNP) concentrations. Lancet 2000 355: 1126.1130.
9. Multiple Sequence Alignment with the Clustal series of programs Nucleic Acids Res (2003) 31 (13): 3497-500.
10. Bowie, J. U et al., (1990). Decipeing the message in Protein Sequences: Tolerance to Amino Acid Substitutions. Science 247, 1306-1310.
11. Harbour and Lane 1998. Antibodies: A Laboratory Manual, Cold Spring Harbour Press New York.$^{27}$
12. Kohler and Milstein 1975. continuous Cultures of Fused Cells Secreting Antibody of Predefined Specificity. Nature, (5517) 256, 495-497.
13. Verhoeyen M. C Milstein, and G Winter Reshaping human antibodies: grafting an antilysozyme activity. Science 1988 Mar. 25; 239(4847):1534-6.
14. Jones, P. T., Dear, P. H., Foote, J., Neuberger, M. S. and Winter, G. "Replacing the complementarity-determining regions in a human antibody with those from a mouse." Nature (1986) 321: 522-525.
15. Riechmann L, Clark M, Waldmann H, Winter G. Reshaping human antibodies for therapy. Nature. 1988 Mar. 24; 332(6162):323-7.
16. Hoogenboom H R, Winter G (1992) Human antibodies from synthetic repertoires of germline VH gene segments rearranged in vitro. J Mol. Biol. 1992 Sep. 20; 227 (2):381-8.
17. Michael Neuberger (1996) Generating high-avidity human Mabs in mice Nature Biotechnology 14, 826
18. Tristan J. Vaughan, Jane K. Osbourn & Philip R. Tempest (1998) Human antibodies by design. Nature Biotechnology 16, 535-539
19. Milstein and Cuello (1983) The co-expression of two immunoglobulin heavy-chain/light-chain pairs, where the two heavy chains have different specificities, Nature, 305: 537-539.
20. Suresh, M. R., Cuello, A. C. and Milstein, C. (1986) Bi-specific monoclonal antibodies from hybrid hybridomas. Methods in Enzymology, 121: 210-228.
21. Brennan et al., "Preparation of bispecific antibodies by chemical recombination of monoclonal immunoglobulin G1 fragments" Science 229:81-83 (1985).
22. Hunt P J, Richards A M, Nicholls M G, Yandle T G, Doughty R N, Espiner E A. Immunoreactive amino terminal pro brain natriuretic peptide (NT-proBNP): a new marker of cardiac impairment. Clin. Endocrinol. 1997 47:287-296.
23. The Immunoassay Handbook. 3$^{rd}$ edition, ed. David Wild. Elsevier Ltd, 2005.
24. Solber H. Approved recommendation (1987) on the theory of reference values. Part 5. Statistical treatment of collected reference values. Determination of reference limits. Journal of clinical Chemistry and Cilinical Biochemistry 1987 25:645-656.
25. Braud V M, Allan D S, O'Callaghan C A, Soderstrom K, D'Andrea A, Ogg G S, Lazetic S, Young N T, Bell J I, Phillips J R, Lanier L L, McMichael A J. HLA-E binds to natural killer cell receptors CD94/NKG2A, B and C. Nature 1998 391:795-799.
26. Universal definition of myocardial infarction. Consensus statement from the Joint ESC/ACCF/AHA/WHF Taskforce for the redefinition of myocardial infarction. Circulation 2007 116:2634-2653.
27. National Academy of Clinical Biochemistry and TFCC Committee for standardisation of markers of cardiac damage laboratory medicine practice guidelines: analytical issues for biochemical markers of acute coronary syndromes. Circulation 2007 115:e352-e355.
28. Kunkel, Thomas A. Rapid and efficient site-specific mutagenesis without phenotypic selection. *Proc. Natl. Acad. Sci. USA Vol.* 82, pp. 488-492, January 1985.
29. Techniques in Protein Modification By Roger L. Lundblad Edition: 2 Published by CRC Press, 1995 288 pages.
30. Atherton et al. (1989) Solid Phase Synthesis: a practical approach, IRL press.
31. Pöykkö S M, Kellokoski E, Hörkkö S, Kauma H, Kesäniemi Y A, Ukkola O. Low plasma ghrelin is associated with insulin resistance, hypertension, and the prevalence of type 2 diabetes. Diabetes. 2003 October; 52(10):2546-53.

The present invention is not limited by the aforementioned particular preferred embodiments. It will occur to those ordinarily skilled in the art that various modifications may be made to the disclosed preferred embodiments with-out diverting from the concept of the invention. All such modifications are intended to be within the scope of the present invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein.

Under no circumstances may the patent be interpreted to be limited by any statement made by any Examiner or any other official or employee of a Patent Office unless such statement is specifically and without qualification or reservation expressly adopted in a responsive writing by Applicants.

The invention claimed is:

1. An assay for a ghrelin signal peptide (SEQ ID NO:15) fragment, comprising:
   (a) binding one or more immunoreactive ghrelin signal peptides from a biological sample, wherein the biological sample is blood, plasma or serum; and
   (b) measuring the level of bound immunoreactive GRN-SP.

2. An assay according to claim 1 wherein the level of immunoreactive ghrelin signal peptide is measured using mass spectroscopy or an assay selected from RIA, ELISA, immunofluorometric assay and immunoradiometric assay.

3. A method for predicting, diagnosing or monitoring a biological event or disorder in a subject wherein the event or disorder correlates with the release of immunoreactive ghrelin signal peptide into the circulation, the method comprising:
   (a) measuring the level of immunoreactive ghrelin signal peptide in a biological sample from the subject; and
   (b) comparing the level of immunoreactive ghrelin signal peptide with the immunoreactive ghrelin signal peptide level from a control,
   wherein a deviation in the measured level from the control level is indicative of a biological event or disorder that correlates with the release of immunoreactive ghrelin signal peptide.

4. A method for predicting, diagnosing or monitoring diabetes, or diabetic potential in a subject, the method comprising:
   (a) measuring the level of immunoreactive ghrelin signal peptide in a biological sample from the subject; and
   (b) comparing the level of said immunoreactive ghrelin signal peptide with the immunoreactive ghrelin signal peptide level from a control,
   wherein a measured level of immunoreactive ghrelin signal peptide lower than the control level is indicative of diabetes or a predisposition to diabetes.

5. A method for assessing dysglycemia in a subject, the method comprising:
   (a) measuring the level of immunoreactive ghrelin signal peptide in a subject after administration of glucose; and
   (b) comparing the level of said immunoreactive ghrelin signal peptide with the immunoreactive ghrelin signal peptide level from a control,
   wherein a deviation in the measured level of immunoreactive ghrelin signal peptide from the control level is indicative of a glucose handling disorder.

6. A method for predicting, diagnosing or monitoring an acute cardiac disorder (ACD) in a subject, the method comprising:

(a) measuring the level of immunoreactive ghrelin signal peptide in a biological sample from the subject; and
(b) comparing the level of said immunoreactive ghrelin signal peptide with the immunoreactive GRN-SP level from a control, wherein a measured level of immunoreactive ghrelin signal peptide higher than the control level is indicative of ACD.

7. A method of claim 6, the method comprising measuring the level of immunoreactive ghrelin signal peptide in a biological sample from the subject within about the first six hours, four hours or two hours of onset of, or clinical presentation with ACD.

8. A method according to claim 6 wherein a level of immunoreactive ghrelin signal peptide in the sample in the range 65 to 250 pmol/L, 65 to 200 pmol/L, 70 to 150, or 70 to 130 pmol/L, is indicative of ACD.

9. A method according to claim 6 wherein a level of immunoreactive ghrelin signal peptide in the sample which is 1.5 to 5, or 2 to 3 times higher than the control level is indicative of ACD.

10. A method according to claim 6 wherein the acute cardiac disorder is an acute myocardial infarction with ST-elevation on presenting ECG, unstable angina, an acute non ST-elevated myocardial infarction; cardiac ischemia, acute cardiac injury, acute cardiac damage resulting from acute drug toxicity, an acute cardiomyopathy, or a cardiac transplant rejection episode.

11. A method according to claim 6 which further comprises measuring the level of one or more non-ghrelin signal peptide markers of said ACD, and comparing the levels against marker levels from a control wherein a deviation in the measured level from the control level, together with a measured level of ghrelin signal peptide which is higher than the control level of ghrelin signal peptide, is predictive or diagnostic of the ACD, or is used to monitor said ACD.

12. A method as claimed in claim 11 wherein the one or more non-ghrelin signal peptide markers are selected from the group consisting of troponin T, troponin I, creatine kinase-MB, myoglobin, ANP, ANP-SP, BNP, NT-BNP, BNP-SP, LDH, aspartate aminotransferase, H-FABP, ischemia modified albumin, endothelin, adrenomedullin, renin and angiotensin II.

13. A method according to claim 4 which further comprises measuring the level of one or more non-ghrelin signal peptide markers of diabetes and comparing the levels against marker levels from a control wherein a deviation in the measured level from the control level of non-ghrelin signal peptide marker, together with a measured level of ghrelin signal peptide which is lower than the control level of ghrelin signal peptide, is predictive or diagnostic of diabetes or can be used to monitor diabetes.

14. A method as claimed in claim 13 wherein the non-ghrelin signal peptide markers are selected from the group consisting of glucose, insulin, lactate, triglycerides and fatty acids or markers therefor.

15. A method according to claim 4, wherein said ghrelin signal peptide fragment is GHR-SP (1-9) (SEQ ID NO:17).

16. A method according to claim 6, wherein said ghrelin signal peptide fragment is GHR-SP (1-9) (SEQ ID NO:17).

17. A method according to claim 4, wherein the biological sample is a sample from a circulatory source.

18. A method according to claim 17, wherein the sample is blood, plasma or serum.

19. A method according to claim 6, wherein the biological sample is a sample from a circulatory source.

20. A method according to claim 19, wherein the sample is blood, plasma or serum.

21. A method according to claim 4, wherein the biological sample is a blood, plasma, serum, saliva, interstitial fluid, urine or heart tissue sample.

22. A method according to claim 6, wherein the biological sample is a blood, plasma, serum, saliva, interstitial fluid, urine or heart tissue sample.

23. A method according to claim 4, wherein the level of immunoreactive ghrelin signal peptide is measured using mass spectroscopy.

24. A method according to claim 23, wherein the mass spectroscopy is selected from the group consisting of SELDI, ESI, MALDI and FTICR.

25. A method according to claim 6, wherein the level of immunoreactive ghrelin signal peptide is measured using mass spectroscopy.

26. An assay according to claim 25, wherein the mass spectroscopy is selected from the group consisting of SELDI, ESI, MALDI and FTICR.

27. A method according to claim 4, wherein the level of immunoreactive ghrelin signal peptide is measured by immunoassay.

28. A method according to claim 27, wherein said immunoassay is selected from the group consisting of an RIA, ELISA, fluoroimmunoassay, immunofluorometric assay, and immunoradiometric assay.

29. A method according to claim 4, wherein the level of immunoreactive ghrelin signal peptide is measured by immunoassay.

30. A method according to claim 29, wherein said immunoassay is selected from the group consisting of an RIA, ELISA, fluoroimmunoassay, immunofluorometric assay, and immunoradiometric assay.

31. A method according to claim 4, wherein the measuring step comprises binding GRN-SP (1-9) (SEQ ID NO:17) with an antibody or antigen-binding fragment thereof.

32. A method according to claim 31, wherein the antibody or antigen-binding fragment selectively binds GRN-SP (1-9) (SEQ ID NO:17).

33. A method according to claim 32, wherein the antibody or antigen-binding fragment is labeled with a detectable marker.

34. A method according to any of claim 31, 32, or 33, wherein the antibody or antigen-binding fragment is immobilized on a solid phase.

35. A method according to claim 6, wherein the measuring step comprises binding GRN-SP (1-9) (SEQ ID NO:17) with an antibody or antigen-binding fragment thereof.

36. A method according to claim 35, wherein the antibody or antigen-binding fragment selectively binds GRN-SP (1-9) (SEQ ID NO:17).

37. A method according to claim 36, wherein the antibody or antigen-binding fragment is labeled with a detectable marker.

38. A method according to any of claim 35, 36 or 37, wherein the antibody or antigen-binding fragment is immobilized on a solid phase.

39. A method according to claim 6, wherein said ACD is acute myocardial infarction.

40. A method according to claim 6, wherein said ACD is acute cardiac ischemia.

* * * * *

SEQUENCE LISTING

```
<160> NUMBER OF SEQ ID NOS: 18

<210> SEQ ID NO 1
<211> LENGTH: 117
<212> TYPE: PRT
<213> ORGANISM: Homo sapiens
<300> PUBLICATION INFORMATION:
```

-continued

```
<308> DATABASE ACCESSION NUMBER: NP_057446
<309> DATABASE ENTRY DATE: 2008-02-10
<313> RELEVANT RESIDUES IN SEQ ID NO: (1)..(117)

<400> SEQUENCE: 1

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
        20                  25                  30

Gln Arg Val Gln Gln Arg Lys Glu Ser Lys Lys Pro Pro Ala Lys Leu
    35                  40                  45

Gln Pro Arg Ala Leu Ala Gly Trp Leu Arg Pro Glu Asp Gly Gln
50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln Gln His Ser Gln
                85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 2
<211> LENGTH: 528
<212> TYPE: DNA
<213> ORGANISM: Homo sapiens
<300> PUBLICATION INFORMATION:
<308> DATABASE ACCESSION NUMBER: NM_016362
<309> DATABASE ENTRY DATE: 2008-02-10
<313> RELEVANT RESIDUES IN SEQ ID NO: (1)..(528)

<400> SEQUENCE: 2
acctccgcca ggaactgcag gcccacctgt ctgcaaccca gctgaggcca tgccctcccc      60
agggaccgtc tgcagcctcc tgctcctcgg catgctctgg ctggacttgg ccatggcagg    120
ctccagcttc ctgagccctg aacaccagag agtccagcag agaaaggagt cgaagaagcc    180
accagccaag ctgcagcccc gagctctagc aggctggctc cgcccggaag atggaggtca    240
agcagaaggg gcagaggatg aactggaagt ccggttcaac gccccctttg atgttggaat    300
caagctgtca ggggttcagt accagcagca cagccaggcc ctggggaagt tcttcagga    360 catcctctgg gaagaggcca agaggcccca gccgacaag tgatcgccca caagccttac    420
tcacctctct ctaagtttag aagcgctcat ctggcttttc gcttgcttct gcagcaactc    480
ccacgactgt tgtacaagct caggaggcga ataaatgttc aaactgta                528

<210> SEQ ID NO 3
<211> LENGTH: 117
<212> TYPE: PRT
<213> ORGANISM: Rattus norvegicus
<300> PUBLICATION INFORMATION:
<308> DATABASE ACCESSION NUMBER: NP_067701
<309> DATABASE ENTRY DATE: 2008-02-17
<313> RELEVANT RESIDUES IN SEQ ID NO: (1)..(117)

<400> SEQUENCE: 3

Met Val Ser Ser Ala Thr Ile Cys Ser Leu Leu Leu Ser Met Leu
1               5                   10                  15

Trp Met Asp Met Ala Met Ala Gly Ser Ser Phe Leu Ser Pro Glu His
        20                  25                  30

Gln Lys Ala Gln Gln Arg Lys Glu Ser Lys Lys Pro Pro Ala Lys Leu
    35                  40                  45
```

```
Gln Pro Arg Ala Leu Glu Gly Trp Leu His Pro Glu Asp Arg Gly Gln
    50                  55                  60

Ala Glu Glu Ala Glu Glu Leu Glu Ile Arg Phe Asn Ala Pro Phe
65                  70                  75                  80

Asp Val Gly Ile Lys Leu Ser Gly Ala Gln Tyr Gln Gln His Gly Arg
                85                  90                  95

Ala Leu Gly Lys Phe Leu Gln Asp Ile Leu Trp Glu Glu Val Lys Glu
                100                 105                 110

Ala Pro Ala Asn Lys
        115

<210> SEQ ID NO 4
<211> LENGTH: 501
<212> TYPE: DNA
<213> ORGANISM: Rattus norvegicus
<300> PUBLICATION INFORMATION:
<308> DATABASE ACCESSION NUMBER: NM_021669
<309> DATABASE ENTRY DATE: 2008-02-17
<313> RELEVANT RESIDUES IN SEQ ID NO: (1)..(501)

<400> SEQUENCE: 4
tccagatcat ctgtcctcac caccaaggcc atggtgtctt cagcgactat ctgcagtttg      60
ctactcctca gcatgctctg gatggacatg gccatggcag gttccagctt cttgagccca     120
gagcaccaga aagcccagca gagaaaggaa tccaagaagc caccagctaa actgcagcca     180
cgagctctgg aaggctggct ccacccagag gacagaggac aagcagaaga ggcagaggag     240
gagctggaaa tcaggttcaa tgctcccttc gatgttggca tcaagctgtc aggagctcag     300
taccagcagc atggccgggc cctgggaaag tttcttcagg atatcctctg ggaagaggtc     360
aaagaggcgc cagctaacaa gtaaccactg acaggactgg tccctgtact ttcctcctaa     420
gcaagaactc acatccagct tctgcctcct ctgcaactcc cagcactctc ctgctgactt     480
acaaataaat gttcaagctg t                                               501

<210> SEQ ID NO 5
<211> LENGTH: 116
<212> TYPE: PRT
<213> ORGANISM: Ovis aries
<300> PUBLICATION INFORMATION:
<308> DATABASE ACCESSION NUMBER: NP_001009721
<309> DATABASE ENTRY DATE: 2007-09-25
<313> RELEVANT RESIDUES IN SEQ ID NO: (1)..(116)

<400> SEQUENCE: 5

Met Pro Ala Pro Arg Thr Ile Tyr Ser Leu Leu Leu Ser Leu Leu
1               5                   10                  15

Trp Met Asp Leu Ala Met Ala Gly Ser Ser Phe Leu Ser Pro Glu His
                20                  25                  30

Gln Lys Leu Gln Arg Lys Glu Pro Lys Lys Pro Ser Gly Arg Leu Lys
                35                  40                  45

Pro Arg Ala Leu Glu Gly Gln Phe Asp Pro Asp Val Gly Ser Gln Glu
        50                  55                  60

Glu Gly Ala Glu Asp Glu Leu Glu Ile Arg Phe Asn Ala Pro Phe Asn
65                  70                  75                  80

Ile Gly Ile Lys Leu Ser Gly Ala Gln Ser Leu Gln His Gly Gln Thr
                85                  90                  95

Leu Gly Lys Phe Leu Gln Asp Ile Leu Trp Glu Glu Ala Glu Glu Thr
                100                 105                 110

Leu Ala Asp Glu
```

<210> SEQ ID NO 6
<211> LENGTH: 531
<212> TYPE: DNA
<213> ORGANISM: Ovis aries
<300> PUBLICATION INFORMATION:
<308> DATABASE ACCESSION NUMBER: NM_001009721
<309> DATABASE ENTRY DATE: 2007-09-25
<313> RELEVANT RESIDUES IN SEQ ID NO: (1)..(531)

<400> SEQUENCE: 6

```
tcgtcctccg cccggaaccc caggtccatc tgcctccagc cagggaagcc atgcccgccc      60
cgcggaccat ctacagcctg ctgctgctca gcctgctctg gatggacttg gccatggcgg     120
gctccagctt tctgagccct gaacatcaga aactgcagag aaaggaacct aagaagccgt     180
caggcagact gaagccccgg gccctggaag gccagtttga cccggatgtg ggaagtcagg     240
aggaaggtgc agaggacgag ctggaaatcc ggttcaatgc ccccctttaac attgggatca     300
agctgtcagg ggctcagtcc ctccagcacg gccagactct ggggaagttt cttcaggaca     360
ttctttggga agaagccgaa gaaacccctgg ctgacgagtg accagccctc ggaccaacca     420
cctgtctgtt ctcccgccct cagaagctct cacctggctt ccgggacact tccgagacca     480
cgtgcagctc tgaggggtac tagcctagga ggtgaataaa tactcaaacg g             531
```

<210> SEQ ID NO 7
<211> LENGTH: 118
<212> TYPE: PRT
<213> ORGANISM: Sus scrofa
<300> PUBLICATION INFORMATION:
<308> DATABASE ACCESSION NUMBER: NP_998972
<309> DATABASE ENTRY DATE: 2007-09-25
<313> RELEVANT RESIDUES IN SEQ ID NO: (1)..(118)

<400> SEQUENCE: 7

```
Met Pro Ser Thr Gly Thr Ile Cys Ser Leu Leu Leu Ser Val Leu
1               5                   10                  15

Leu Met Ala Asp Leu Ala Met Ala Gly Ser Ser Phe Leu Ser Pro Glu
            20                  25                  30

His Gln Lys Val Gln Gln Arg Lys Glu Ser Lys Lys Pro Ala Ala Lys
        35                  40                  45

Leu Lys Pro Arg Ala Leu Glu Gly Trp Leu Gly Pro Glu Asp Ser Gly
    50                  55                  60

Glu Val Glu Gly Thr Glu Asp Lys Leu Glu Ile Arg Phe Asn Ala Pro
65                  70                  75                  80

Cys Asp Val Gly Ile Lys Leu Ser Gly Ala Gln Ser Asp Gln His Gly
                85                  90                  95

Gln Pro Leu Gly Lys Phe Leu Gln Asp Ile Leu Trp Glu Glu Val Thr
            100                 105                 110

Glu Ala Pro Ala Asp Lys
        115
```

<210> SEQ ID NO 8
<211> LENGTH: 509
<212> TYPE: DNA
<213> ORGANISM: Sus scrofa
<300> PUBLICATION INFORMATION:
<308> DATABASE ACCESSION NUMBER: NM_213807
<309> DATABASE ENTRY DATE: 2007-09-25
<313> RELEVANT RESIDUES IN SEQ ID NO: (1)..(509)

<400> SEQUENCE: 8

```
agccaggaag accagctgag gccatgccct ccacggggac catttgcagc ctgctgctcc    60
tcagcgtgct cctcatggca gacttggcca tggcgggctc cagcttcttg agccccgaac   120
accagaaagt gcagcagaga aaggagtcca agaagccagc agccaaactg aagccccggg   180
ccctggaagg ctggctcggc ccagaagaca gtggtgaggt ggaaggcacg gaggacaagc   240
tggaaatccg gttcaacgcc cctgtgatg ttgggatcaa gttgtcaggg gctcagtccg    300
accagcacgg ccagccctg gggaaatttc tccaggacat cctctgggaa gaggtcactg    360
aggccccggc cgacaagtga ttgtccctga ccagccac ctctgttctc ccagcttcct     420
aagggctcac ctggcttcca ggacgcttcc actatcacac ccagctctga gggacgctag   480
cctgggaggt gaataaacat tcagactgg                                    509
```

<210> SEQ ID NO 9
<211> LENGTH: 117
<212> TYPE: PRT
<213> ORGANISM: Mus musculus
<300> PUBLICATION INFORMATION:
<308> DATABASE ACCESSION NUMBER: NP_067463
<309> DATABASE ENTRY DATE: 2008-03-02
<313> RELEVANT RESIDUES IN SEQ ID NO: (1)..(117)

<400> SEQUENCE: 9

```
Met Leu Ser Ser Gly Thr Ile Cys Ser Leu Leu Leu Leu Ser Met Leu
1               5                   10                  15

Trp Met Asp Met Ala Met Ala Gly Ser Ser Phe Leu Ser Pro Glu His
            20                  25                  30

Gln Lys Ala Gln Gln Arg Lys Glu Ser Lys Lys Pro Pro Ala Lys Leu
        35                  40                  45

Gln Pro Arg Ala Leu Glu Gly Trp Leu His Pro Glu Asp Arg Gly Gln
    50                  55                  60

Ala Glu Glu Thr Glu Glu Leu Glu Ile Arg Phe Asn Ala Pro Phe
65                  70                  75                  80

Asp Val Gly Ile Lys Leu Ser Gly Ala Gln Tyr Gln Gln His Gly Arg
                85                  90                  95

Ala Leu Gly Lys Phe Leu Gln Asp Ile Leu Trp Glu Glu Val Lys Glu
            100                 105                 110

Ala Pro Ala Asp Lys
        115
```

<210> SEQ ID NO 10
<211> LENGTH: 527
<212> TYPE: DNA
<213> ORGANISM: Mus musculus
<300> PUBLICATION INFORMATION:
<308> DATABASE ACCESSION NUMBER: NM_021488
<309> DATABASE ENTRY DATE: 2008-03-02
<313> RELEVANT RESIDUES IN SEQ ID NO: (1)..(527)

<400> SEQUENCE: 10

```
atccccaggc attccaggtc atctgtcctc accaccaaga ccatgctgtc ttcaggcacc    60
atctgcagtt tgctgctact cagcatgctc tggatggaca tggccatggc aggctccagc   120
ttcctgagcc cagagcacca gaaagcccag cagagaaagg aatccaagaa gccaccagct   180
aaactgcagc cacgagctct ggaaggctgg ctccacccag aggacagagg acaagcagaa   240
gagacagagg aggagctgga gatcaggttc aatgctccct cgatgttgg catcaagctg    300 tcaggagctc agtatcagca gcatggccgg gccctgggga gtttcttcca ggatatcctc   360
tgggaagagg tcaaagaggc gccagctgac aagtaaccac ggacaggcct gaccccgtg    420
```

```
ctttccttct cctgagcaag aactcacatc cgcctcagcc tcctcggcaa ctcccagcac      480
tctcctacca ctttaagaat aaatgttcac ctgtatgcca aatgttc                   527
```

<210> SEQ ID NO 11
<211> LENGTH: 117
<212> TYPE: PRT
<213> ORGANISM: Canis familiaris
<300> PUBLICATION INFORMATION:
<308> DATABASE ACCESSION NUMBER: NP_001003052
<309> DATABASE ENTRY DATE: 2007-06-27
<313> RELEVANT RESIDUES IN SEQ ID NO: (1)..(117)

<400> SEQUENCE: 11

```
Met Pro Ser Leu Gly Thr Met Cys Ser Leu Leu Phe Ser Val Leu
1               5                   10                  15

Trp Val Asp Leu Ala Met Ala Gly Ser Ser Phe Leu Ser Pro Glu His
            20                  25                  30

Gln Lys Leu Gln Gln Arg Lys Glu Ser Lys Lys Pro Ala Lys Leu
        35                  40                  45

Gln Pro Arg Ala Leu Glu Gly Ser Leu Gly Pro Glu Asp Thr Ser Gln
    50                  55                  60

Val Glu Glu Ala Glu Asp Glu Leu Glu Ile Arg Phe Asn Ala Pro Phe
65                  70                  75                  80

Asp Val Gly Ile Lys Leu Ser Gly Pro Gln Tyr His Gln His Gly Gln
                85                  90                  95

Ala Leu Gly Lys Phe Leu Gln Glu Val Leu Trp Glu Asp Thr Asn Glu
            100                 105                 110

Ala Leu Ala Asp Glu
        115
```

<210> SEQ ID NO 12
<211> LENGTH: 547
<212> TYPE: DNA
<213> ORGANISM: Canis familiaris
<300> PUBLICATION INFORMATION:
<308> DATABASE ACCESSION NUMBER: NM_001003052
<309> DATABASE ENTRY DATE: 2007-06-27
<313> RELEVANT RESIDUES IN SEQ ID NO: (1)..(547)

<400> SEQUENCE: 12

```
gaattcggca cgaggggaat cccaggcgca tctgacacca tgccctccct ggggaccatg      60
tgcagcctgc tgctcttcag tgtgctctgg gtggacctgg ccatggcggg ctccagcttc     120
ctaagtcccg aacaccagaa actacagcag agaaaggagt ccaagaagcc gccggccaaa     180
ctgcagcccc gagccctaga aggctccctt ggcccagaag acacaagtca agtggaagag     240
gcagaggatg agctggaaat ccggttcaat gccccctttg atgttggaat caagctgtca     300
gggcctcagt accaccagca tggccaggca ctcgggaagt tcttcaaga ggttctttgg      360 gaagacacca cgaggccct ggcagacgag tgatcatcca agatgggc ctgcctgttc        420 tcccccacc ctagaagcac tcacctgact tttacactgt ttctgcagct actcccagtt     480
ctgagtggta ctagttgaag aggtgaataa acattcaaac cataaaaaaa aaaaaaaaa     540 actcgag                                                               547
```

<210> SEQ ID NO 13
<211> LENGTH: 116
<212> TYPE: PRT
<213> ORGANISM: Felis catus
<300> PUBLICATION INFORMATION:
<308> DATABASE ACCESSION NUMBER: NP_001009853
<309> DATABASE ENTRY DATE: 2007-09-03

<313> RELEVANT RESIDUES IN SEQ ID NO: (1)..(116)

<400> SEQUENCE: 13

Met Pro Ser Pro Gly Thr Val Cys Ser Leu Leu Leu Phe Ser Met Leu
1               5                   10                  15

Trp Ala Asp Leu Ala Met Ala Gly Ser Ser Phe Leu Ser Pro Glu His
            20                  25                  30

Gln Lys Val Gln Arg Lys Glu Ser Lys Lys Pro Pro Ala Lys Leu Gln
        35                  40                  45

Pro Arg Ala Leu Glu Gly Leu Ile His Pro Glu Asp Thr Ser Gln Val
    50                  55                  60

Glu Gly Ala Glu Asp Glu Leu Glu Ile Arg Phe Asn Ala Pro Phe Asp
65                  70                  75                  80

Val Gly Ile Lys Leu Ser Gly Ala Gln Tyr His Gln His Gly Gln Ala
                85                  90                  95

Leu Gly Lys Phe Leu Gln Asp Val Leu Trp Glu Glu Ala Asp Glu Val
            100                 105                 110

Leu Ala Asp Glu
        115

<210> SEQ ID NO 14
<211> LENGTH: 640
<212> TYPE: DNA
<213> ORGANISM: Felis catus
<220> FEATURE:
<221> NAME/KEY: misc_feature
<222> LOCATION: (69)..(69)
<223> OTHER INFORMATION: n is a, c, g, or t
<300> PUBLICATION INFORMATION:
<308> DATABASE ACCESSION NUMBER: NM_001009853
<309> DATABASE ENTRY DATE: 2007-09-03
<313> RELEVANT RESIDUES IN SEQ ID NO: (1)..(640)

<400> SEQUENCE: 14
ggcagagaga aagggagaga tcgagaatcc caagcagcat ggagcttgat gcagggatcg      60
aactcatgng actgtgagat catgacctga gctgaaacca agaatcagat gcttaactga     120
cttccaccag gaatcccagg cccacctgac accatgccct ccccggggac cgtgtgcagc     180
ctgctgctct tcagcatgct gtgggcagac ttggccatgg caggctccag cttcctgagc     240
cccgaacacc agaaagtaca gagaaaggaa tccaagaagc caccagccaa actgcagccc     300
cgagctctgg aaggcttgat ccacccagaa gacacaagtc aagtggaagg ggcagaggat     360
gaactagaaa tccggttcaa cgccccttt gatgttggaa tcaagctgtc aggggctcag     420
taccaccagc atggccaggc gctggggaag tttcttcagg acgtcctttg ggaagaggcc     480
gatgaggtcc tggcagatga gtgatcatcc actagaacga cccacttgcc ttcctcccaa     540
cctgacagcg cccacctggc ttttaaactg tttctgcaac aacatccagt tctgagtggt     600
actagcttaa gaagtgtata aacattcatg ctgtatgccg                           640

<210> SEQ ID NO 15
<211> LENGTH: 23
<212> TYPE: PRT
<213> ORGANISM: Homo sapiens
<300> PUBLICATION INFORMATION:
<308> DATABASE ACCESSION NUMBER: NP_057446
<309> DATABASE ENTRY DATE: 2008-02-10
<313> RELEVANT RESIDUES IN SEQ ID NO: (1)..(23)

<400> SEQUENCE: 15

Met Pro Ser Pro Gly Thr Val Cys Ser Leu Leu Leu Leu Gly Met Leu
1               5                   10                  15

```
Trp Leu Asp Leu Ala Met Ala
         20

<210> SEQ ID NO 16
<211> LENGTH: 69
<212> TYPE: DNA
<213> ORGANISM: Homo sapiens
<300> PUBLICATION INFORMATION:
<308> DATABASE ACCESSION NUMBER: NM_016362
<309> DATABASE ENTRY DATE: 2008-02-10
<313> RELEVANT RESIDUES IN SEQ ID NO: (1)..(69)

<400> SEQUENCE: 16
atgccctccc cagggaccgt ctgcagcctc ctgctcctcg gcatgctctg gctggacttg    60
gccatggca                                                            69

<210> SEQ ID NO 17
<211> LENGTH: 9
<212> TYPE: PRT
<213> ORGANISM: Homo sapiens
<300> PUBLICATION INFORMATION:
<308> DATABASE ACCESSION NUMBER: NP_057446
<309> DATABASE ENTRY DATE: 2008-02-10
<313> RELEVANT RESIDUES IN SEQ ID NO: (1)..(9)

<400> SEQUENCE: 17

Met Pro Ser Pro Gly Thr Val Cys Ser
1               5

<210> SEQ ID NO 18
<211> LENGTH: 27
<212> TYPE: DNA
<213> ORGANISM: Homo sapiens
<300> PUBLICATION INFORMATION:
<308> DATABASE ACCESSION NUMBER: NM_016362
<309> DATABASE ENTRY DATE: 2008-02-10
<313> RELEVANT RESIDUES IN SEQ ID NO: (1)..(27)

<400> SEQUENCE: 18
atgccctccc cagggaccgt ctgcagc                                        27
```